US012714562B2

(12) United States Patent
Pham et al.

(10) Patent No.: US 12,714,562 B2
(45) Date of Patent: Aug. 25, 2026

(54) TRANSCATHETER VALVE LEAFLET REPLACEMENT DEVICE, DELIVERY, GUIDING AND FIXATION SYSTEM AND METHOD FOR SAME

(71) Applicant: DURA LLC, Marietta, GA (US)

(72) Inventors: Thuy Pham, Marietta, GA (US); Caitlin Martin, Marietta, GA (US); Nur Hamideh, Marietta, GA (US)

(73) Assignee: Sutra Medical, Inc., Lake Forest, CA (US)

(*) Notice: Subject to any disclaimer, the term of this patent is extended or adjusted under 35 U.S.C. 154(b) by 1364 days.

(21) Appl. No.: 17/198,097

(22) Filed: Mar. 10, 2021

(65) Prior Publication Data

US 2021/0212825 A1 Jul. 15, 2021

Related U.S. Application Data

(63) Continuation-in-part of application No. 17/121,615, filed on Dec. 14, 2020, which is a continuation of
(Continued)

(51) Int. Cl.
*A61F 2/24* (2006.01)
*A61F 2/966* (2013.01)

(52) U.S. Cl.
CPC .......... *A61F 2/2436* (2013.01); *A61F 2/2418* (2013.01); *A61F 2/9661* (2020.05);
(Continued)

(58) Field of Classification Search
CPC ...... A61F 2220/0016; A61F 2220/0008; A61F 2230/0091; A61F 2230/0013;
(Continued)

(56) References Cited

U.S. PATENT DOCUMENTS 5,201,757 A * 4/1993 Heyn ........................ A61F 2/95 606/198
2005/0251162 A1 * 11/2005 Rothe .................. A61B 1/0014 606/153
(Continued)

*Primary Examiner* — Sarah A Long
*Assistant Examiner* — Lauren Dubose
(74) *Attorney, Agent, or Firm* — William A. English; Vista IP Law Group LLP

(57) ABSTRACT

A transcatheter heart valve leaflet replacement system includes a valve prosthesis and a multi-stage, multi-lumen (MSML) heart valve delivery and implantation system for guiding and implanting the prosthesis to a native annulus. The prosthesis includes a stent frame including an upper atrial flared portion and a lower ventricular portion, a plurality of prosthetic leaflets, and at least one lining skirt. The prosthesis is configurable or otherwise sizable to fit in the MSML delivery and implantation system and to subsequently be selectively expanded to an operative size and position once deployed within the annulus. A portion of the prosthesis can be configured to couple with dual guiding and fixation (DGF) members to guide and fix the prosthesis to the annulus. In one aspect, the MSML delivery and implantation system includes a main docking system, a DGF member delivery system, and a valve housing, positioning, and locking system.

20 Claims, 9 Drawing Sheets

Related U.S. Application Data application No. PCT/US2019/037476, filed on Jun. 17, 2019, application No. 17/198,097 is a continuation-in-part of application No. 15/453,518, filed on Mar. 8, 2017, now Pat. No. 11,007,057.

(60) Provisional application No. 62/988,253, filed on Mar. 11, 2020, provisional application No. 62/685,378, filed on Jun. 15, 2018, provisional application No. 62/427,551, filed on Nov. 29, 2016, provisional application No. 62/413,693, filed on Oct. 27, 2016, provisional application No. 62/305,204, filed on Mar. 8, 2016.

(52) U.S. Cl.
CPC ................. *A61F 2220/0016* (2013.01); *A61F 2230/0091* (2013.01)

(58) Field of Classification Search
CPC .... A61F 2/2436; A61F 2/9661; A61F 2/2418; A61F 2/2466; A61F 2/2454; A61F 2/2427; A61F 2/246; A61F 2002/9665; A61F 2/2463; A61B 2017/0649; A61B 2017/0409; A61B 2017/0412; A61B 2017/0488; A61B 2017/0427; A61B 2017/0429; A61B 2017/0437; A61B 2017/0448; A61B 17/0401; A61B 17/0487; A61B 2017/0414; A61B 2017/045
See application file for complete search history.

(56) References Cited

U.S. PATENT DOCUMENTS

| | | | | |
|---|---|---|---|---|
| 2007/0213813 | A1* | 9/2007 | Von Segesser | A61F 2/2427 623/2.11 |
| 2008/0228266 | A1* | 9/2008 | McNamara | A61F 2/2445 623/2.36 |
| 2011/0015616 | A1* | 1/2011 | Straubinger | A61F 2/2436 604/528 |
| 2011/0106245 | A1* | 5/2011 | Miller | A61F 2/2442 623/2.11 |
| 2011/0166649 | A1* | 7/2011 | Gross | A61F 2/2466 623/2.36 |
| 2012/0022639 | A1* | 1/2012 | Hacohen | A61F 2/2436 623/2.11 |
| 2014/0018906 | A1* | 1/2014 | Rafiee | A61F 2/2427 623/1.26 |
| 2014/0330368 | A1* | 11/2014 | Gloss | A61F 2/243 623/2.11 |
| 2014/0371844 | A1* | 12/2014 | Dale | A61F 2/2436 623/2.11 |
| 2015/0366556 | A1* | 12/2015 | Khairkhahan | A61F 2/2454 606/232 |
| 2015/0366666 | A1* | 12/2015 | Khairkhahan | A61F 2/2454 623/2.11 |

* cited by examiner

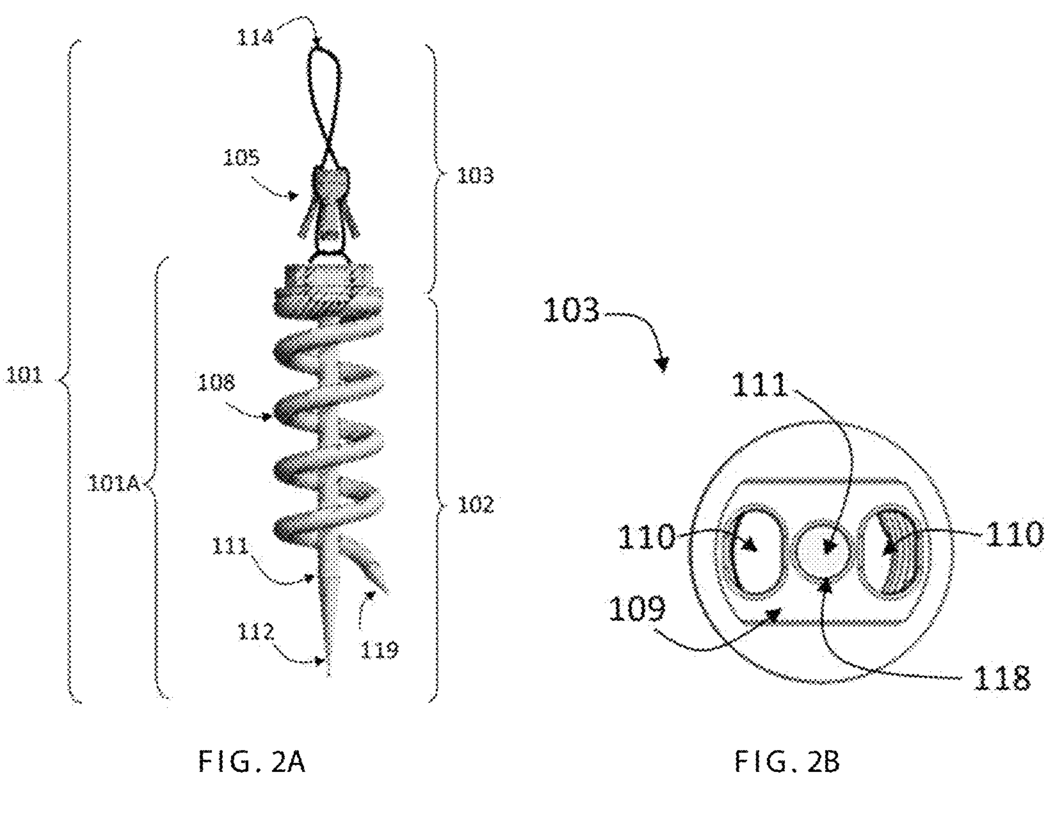
FIG. 2A
FIG. 2B
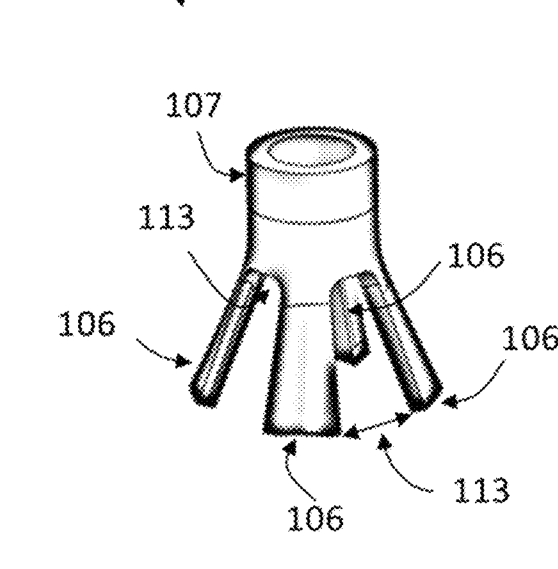
FIG. 2C 306
317
201
101
101
101
2

306
317
2
201

306
317
2
201

306
317
201

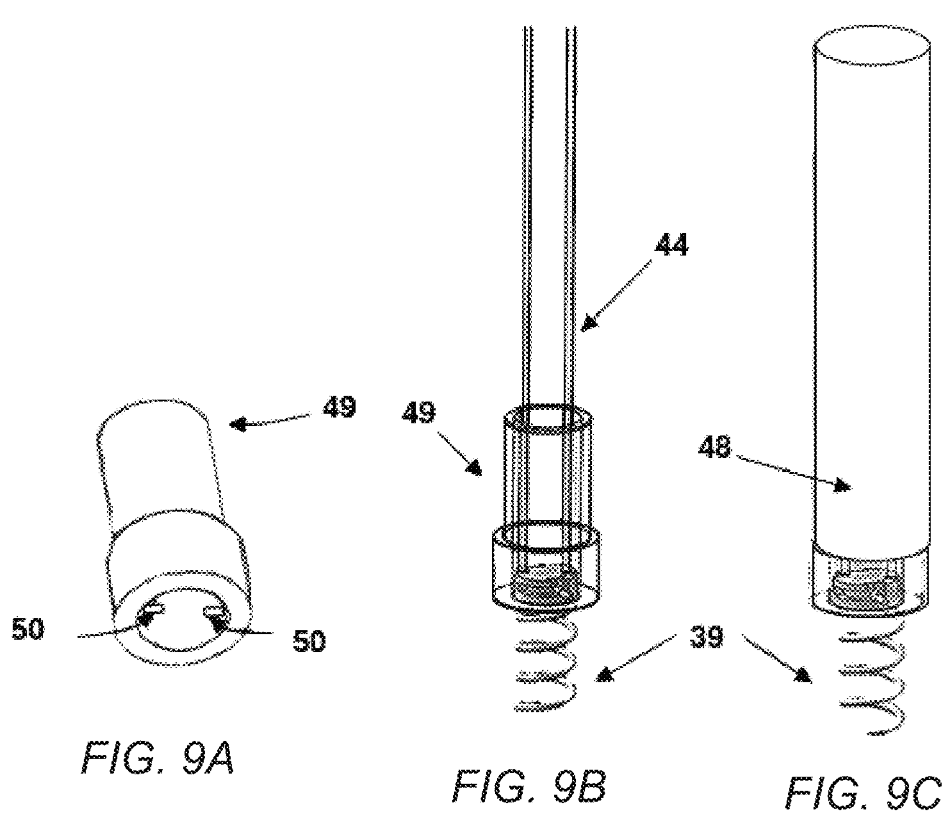
FIG. 9A
FIG. 9B
FIG. 9C
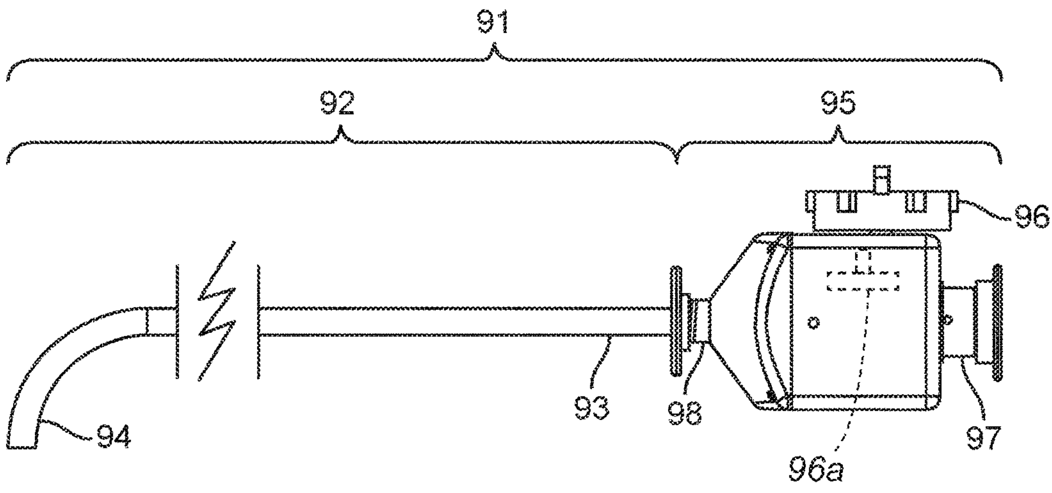
FIG. 10

TRANSCATHETER VALVE LEAFLET REPLACEMENT DEVICE, DELIVERY, GUIDING AND FIXATION SYSTEM AND METHOD FOR SAME

CROSS REFERENCE TO RELATED APPLICATIONS

This application claims benefit of U.S. provisional application Ser. No. 62/988,253, filed Mar. 11, 2020, and is a continuation-in-part of co-pending application Ser. No. 15/453,518, filed Mar. 8, 2017, which claims benefit of U.S. provisional applications Ser. No. 62/305,204, filed Mar. 8, 2016, 62/413,693, filed Oct. 27, 2016, and 62/427,551, filed Nov. 29, 2016, and is a continuation-in-part of co-pending application Ser. No. 17/121,615, filed Dec. 14, 2020, which is a continuation of International application No. PCT/US2019/037476, filed Jun. 17, 2019, which claims benefit of U.S. Provisional Application No. 62/685,378, filed Jun. 15, 2018, which disclosures, including specification and drawings, are all hereby incorporated herein in their entirety by reference.

FIELD OF THE INVENTION

The application relates generally to a heart valve replacement system and transcatheter implantation of prosthetic heart valves, e.g., for replacing diseased mitral and/or tricuspid valves in humans or animals. More particularly, embodiments of the subject matter relate to a tissue-based valve leaflet replacement system and methods to operatively deliver and secure the leaflet replacement valve in its target position.

BACKGROUND

The mitral valve (MV) sits between the left atrium (LA) and the left ventricle (LV) of a human heart and normally consists of a mitral annulus (MA), two leaflets, chordae tendineae ("chords"), two papillary muscles, and the left ventricular myocardium. The mitral annulus is subdivided into an anterior portion and a posterior portion.

When the mitral valve is closed, the respective anterior and posterior leaflets are in close contact to form a single zone of apposition. As one skilled in the art will appreciate, normal MV function involves a proper force balance, with each of its components working congruently during a cardiac cycle. Pathological alterations affecting any of the components of the MV, such as chord rupture, annulus dilatation, papillary muscle displacement, leaflet calcification, and myxomatous disease, can lead to altered MV function and cause mitral valve regurgitation (MR).

Mitral regurgitation is dysfunction of the MV that causes an abnormal leakage of blood from the LV back into the left atrium during systole (i.e., the expulsion phase of the heart cycle in which blood moves from the LV into the aorta).

The current treatments for MV diseases include surgical repair and replacement of the MV, and more recently, transcatheter repair and replacement of the MV.

The noted challenges to an efficacious MV replacement device generally include operative delivery challenges; positioning and fixation challenges; seal and paravalvular leakage challenges; and hemodynamic function challenges such as left ventricle outflow tract (LVOT) obstruction.

With respect to the noted operative delivery challenges, since a conventional mitral prosthesis is larger than a conventional aortic prosthesis, it is more difficult to fold and compress the larger mitral prosthesis into a catheter for deployment as well as retrieval through either conventional trans-apical or trans-femoral delivery techniques.

Turning to the positioning and implantation challenges, instability and migration are the most prominent obstacles given that the mitral valve is subjected to high and repetitive loads in a cardiac cycle, with a high transvalvular pressure gradient and dynamic motion of the beating heart.

With respect to sealing and paravalvular leakage, since the mitral valve annulus is large, a good fit between the native annulus and the prosthesis that minimizes paravalvular leak is desirable. Typically, a prosthetic mitral valve may have a large overhanging atrial portion or flare which can prevent leakage, but, problematically, it also requires a large valve size at the ventricular level so that the prosthesis can be tightly fitted in the native MV. Conventionally, a prosthetic mitral valve is smaller than the diseased native valve and additional material is added around the prosthetic valve to compensate for the large native mitral annulus. Undesirably, adding more material to a prosthetic valve increases the size of the delivery system and may cause valve thrombosis.

Some of the current transcatheter delivery systems utilize folding structures of the replacement valve stent to capture and grab the native leaflets and annulus to anchor the replacement valve. Such methods frequently suffer from the dislodgement of the device due to either insufficient interactive force between the implant and the native tissue, or excess interactive force that leads to native tissue damage (e.g., tearing) and/or remodeling (e.g., elongation, reshaping), which causes the instability and/or migration of the implant.

Finally, with respect to the preservation of hemodynamic function, the operative positioning of a prosthetic mitral valve device, which is conventionally large as described above, should not obstruct the LVOT at the anterior portion of the mitral annulus and should not interfere with the associated structures of a native aortic and/or mitral valve.

Accordingly, it would be beneficial to have a heart valve leaflet replacement device and delivery and implantation system that does not suffer from the shortcomings and deficiencies of current systems. It is desirable to secure the prosthetic mitral valve replacement system to the native mitral annulus. It is also desirable to improve positioning of a mitral prosthesis, avoid LVOT obstruction, and prevent leaking of blood between the mitral prosthesis and the native MV. Furthermore, other desirable features and characteristics will become apparent from the subsequent detailed description and the appended claims, taken in conjunction with the accompanying drawings and the foregoing technical field and background.

SUMMARY

Described herein is a heart valve leaflet replacement system that includes a heart valve leaflet replacement device (e.g., a prosthetic mitral valve replacement device) and a multi-stage, multi-lumen (MSML) heart valve delivery and implantation system for guiding and fixation of the heart valve leaflet replacement device to one or more of the native annuli. In one aspect, the MSML heart valve delivery and implantation system can be configured to guide and fix the mitral valve replacement device to the native mitral annulus. In another aspect, the MSML heart valve delivery and implantation system can be configured to guide and fix the prosthetic tricuspid valve replacement device to the native tricuspid annulus. For clarity, it will be appreciated that this disclosure will focus on the delivery and implantation of valve leaflet replacement devices for the treatment of functional and degenerative mitral regurgitation, however it is contemplated that the valve leaflet replacement device, the MSML delivery and implantation system and the associated methods can be used or otherwise configured to be used to treat other valve disease conditions and replace other valves of the human heart, or could be used or otherwise configured to be used in other mammals or animals suffering from valve deficiencies as well.

In one aspect, the heart valve leaflet replacement system can comprise a heart valve leaflet replacement device, or prosthesis, that is configurable or otherwise sizable to fit in the MSML delivery and implantation system and to subsequently be selectively expanded to an operative size and position once removed from the MSML delivery and implantation system within the heart. In a further aspect, at least a portion of the prosthesis can comprise a stent with an upper atrial flared portion and a lower ventricular portion. In one aspect, the atrial flared portion can be configured to couple with a plurality of dual guiding and fixation (DGF) members to guide and fix the stent on the annulus, which can help prevent paravalvular leakage and dislodgement of the prosthesis after implantation. The lower ventricular portion of the prosthesis can displace a portion of native leaflets out of the blood flow tract and houses at least one prosthetic leaflet. In another aspect, the heart valve leaflet replacement device can comprise a lining skirt that can be coupled to at least a portion of the inner and/or outer surfaces of the stent. Optionally, the outer surfaces of the stent can be configured with additional skirt material to prevent paravalvular leakage. In one exemplary aspect, at least one prosthetic leaflet can be mounted on the inner lumen of the stent and/or on at least a portion of the outer side of the stent, which can function in place of at least one native leaflet to restore normal valve function, e.g., to prevent mitral regurgitation.

In an exemplary embodiment, the MSML delivery system can be configured to implant the heart valve leaflet replacement system in a two-step procedure. In step 1, a plurality of DGF members are implanted into the native annulus of the diseased valve. In step 2, a prosthetic heart valve leaflet replacement device is implanted and secured in position at the implanted DGF members.

It should be apparent to one of ordinary skill in the art that various other prosthetic valve replacement devices, regardless of whether it is a hemi-valve or a full-valve, of circular or non-circular shape, can also be delivered and implanted using the MSML delivery methods described in the present disclosure.

In one aspect, the delivery of the prosthesis can be conducted using several desired delivery access approaches, such as, for example and not meant to be limiting, a minimally invasive surgical, a trans-septal, or a trans-atrial approach. In one exemplary aspect, the trans-septal approach can comprise creating an opening in the internal jugular or femoral vein for the subsequent minimally invasive delivery of portions of the heart valve leaflet replacement device, or a prosthetic device, through the superior or inferior vena cava, which flow into the right atrium of the heart. In this exemplary aspect, the access path of the trans-septal approach crosses the atrial septum of the heart, and once achieved, the components of the heart valve leaflet replacement device can operatively be positioned in the left atrium, the native mitral valve, and the left ventricle.

In one aspect, the MSML delivery and implantation system can comprise a main docking/guiding system, a DGF member delivery system and a valve housing, positioning, and locking system (VHPL).

In one exemplary aspect the VHPL can comprise a guide sheath, a plurality of locking catheters, a stent holder sheath, and a valve chamber sheath.

In one aspect, it is contemplated that a main docking sheath can be placed within the access path to allow desired components of the heart valve leaflet replacement system to be operatively positioned with the left atrium without complications.

In one aspect, one component of the heart valve leaflet replacement device can comprise DGF members which can be operatively positioned and implanted at desired locations in the native annulus prior to the delivery of the prosthesis. In this aspect, the DGF members can guide the subsequent precise positioning and fixation of the prosthesis. In a further aspect, the plurality of DGF members can help prevent leakage of blood between the operatively positioned prosthesis and the native mitral annulus. In one aspect, the DGF member can be configured with removable and permanent components, where removable components can aid in guiding the heart valve leaflet replacement device to the operable position, and then be removed from the patient's body after fixing the prosthesis, and permanent components remain in the patient's body to keep the heart valve leaflet replacement device secured to the native annulus.

In an exemplary aspect, the DGF members can comprise multiple sections, such as a head member, a body member and a tail member. In one aspect, the DGF head member can be operatively inserted and embedded in the annular tissue. In one aspect, the DGF body member can be configured with a DGF locking member to fix the heart valve leaflet replacement device to the native mitral annulus. In another aspect, the DGF body member can be configured so that it can be engaged to a catheter, drill the DGF head member into the tissue, and disengage from the catheter to leave the entire DGF member permanently implanted in the annulus. The DGF members are designed to be removable and repositionable. In one aspect, the DGF tail member can be configured as a flexible component that extends from the proximal portion of the DGF body to the proximal end of the MSML system. Optionally, the DGF tail can be configured to be selectively removable, such that it can be removed from the body at the completion of the heart valve leaflet replacement system implantation procedure.

One skilled in the art can appreciate that during an operation, the patient's heart is beating and the annular tissue is moving, thus it can be difficult to 1) engage the annular tissue and 2) maintain proper positioning of the DGF delivery system throughout implantation of a DGF member. In such conditions, it can be considered necessary to have a stabilization member. In this aspect, the DGF head member can be configured with a stabilizer member, e.g., a concentric needle within the DGF head member, that acts to stabilize the DGF member and the DGF member delivery mechanism during DGF member implantation. In one aspect, the stabilizer member can be configured with other mechanisms that can engage and/or disengage the tissue, such as vacuum suction, clamping and release, or other mechanisms due to changes induced by electromagnetic or thermal fields.

In one aspect, the DGF body member can be configured with a prosthetic valve fixation mechanism including a plurality of DGF locking members. In one aspect, the DGF locking members can be configured to engage the prosthetic valve to fix it in the operative position.

In an exemplary aspect, the DGF locking member can be configured to attach to the DGF body member via a flexible component.

The DGF locking member can be configured to engage the DGF tail member.

In one aspect, the prosthesis can be configured to engage the DGF locking member via a plurality of through-holes in the atrial flared portion of the stent frame. In this aspect, the DGF tail member can be a tether that is configured so that one end of the tether is attached to the DGF body member and the other end of the tether can exit the body. Subsequently, the tether can be inserted through the hole on the atrial flared portion of the stent, such that prosthesis can be delivered over the DGF tail members and the atrial flared portion of the stent can be precisely delivered to the DGF body members embedded in the annulus.

In one aspect, the positioning of such DGF members is not random. The spacing of the DGF members on the annulus should be closely matched to the spacing of the through-holes on the prosthetic stent to ensure accurate positioning and placements of the prosthesis within the posterior annulus.

In another aspect, two sets of DGF members can be deployed separately. In this aspect, the initial set of DGF members can be implanted at the proximity of the commissures of the native valve and the middle of the posterior annulus. This set of DGF members will guide the precise positioning and deployment of the prosthesis. After valve deployment, a second set of DGF members can be implanted directly on the top of the deployed prosthesis. In another aspect, the second set of DGF members can be deployed on top of the flare section of the prosthetic stent. One can appreciate that with additional DGF members implanted the posterior annulus, the lesser the gap between the prosthetic and the native annulus, thus, preventing paravalvular leakage and eventually prosthetic valve dehiscence.

In one aspect, the DGF locking member can be configured such that it can selectively be compressed to a diameter smaller than the diameter of the hole on the atrial flared portion of the stent, such that it can pass through the hole, and subsequently be selectively re-expanded to its original size, larger than the diameter of the hole on the flared portion of the stent to prevent backward motion of the DGF locking member through the hole.

In one exemplary aspect, the DGF locking member can be configured with a plurality of radially compressible legs, e.g., forming a cone shape where the proximal tip of the cone shape has a smaller diameter than the hole on the atrial flare of the stent, and the distal base of the cone shape has a larger diameter than the hole on the atrial flare of the stent. In operation, the DGF tails can be tensioned to pull the proximal tips of the DGF locking members into the holes on the atrial flared portion of the stent, and as the locking member legs come into contact with the edges of the holes, will compress radially to allow the DGF locking member to be pulled completely through the holes. Once the locking member has completely passed through the stent, the DGF locking member legs can re-expand to full size to prevent backward motion of the DGF locking member through the holes in the atrial stent flare.

In one aspect, the VHPL system can comprise a guide sheath that fits within the lumen of the docking sheath and can house all the other VHPL system components. In one exemplary aspect, the guide sheath can be configured with a separator at the distal tip, which organizes all the inner tubes and prevents tangling or overlapping of the DGF tails and locking catheters.

In another aspect, the entire guide sheath could be configured with multiple lumens to organize the inner tubes. In one exemplary aspect, the separator can have four lumens: one central lumen surrounded by three outer lumens. The stent holder sheath can go through the center lumen of the separator, and a locking catheter can go through each of the three outer lumens.

In one aspect, the VHPL can comprise a valve chamber. In this aspect, the heart valve leaflet replacement device can be crimped down to fit within a valve chamber on the distal end of the VHPL system, and subsequently be selectively expanded to an operative size and positioned once removed from the valve chamber in the VHPL system.

In one aspect, a stent holder can be configured to fit within the lumen of the valve chamber and to facilitate prosthesis valve release. In this aspect, the stent holder can be configured to attach to the distal tip of a stent holder sheath that extends to the proximal side of the VHPL system, such that the stent holder position within the valve chamber can be controlled by manipulating the stent holder sheath on the proximal side of the VHPL system.

In one aspect, the valve chamber sheath can be configured, steerable or non-steerable, to fit within the lumen of the stent holder sheath. The valve chamber sheath can be optionally configured as a tube or solid rod.

In an exemplary aspect, the stent can be crimped over the stent holder sheath proximal to the stent holder and loaded into the valve chamber. The prosthesis can then be subsequently released from the valve chamber by advancing the valve chamber sheath distally while keeping the stent holder position fixed. The stent holder will prevent distal motion of the prosthesis, and as the valve chamber is moved distally, the prosthetic valve will be released from the valve chamber beginning with the proximal side of the prosthetic valve and ending with the distal side of the prosthetic valve.

In one exemplary aspect, three DGF head members can be implanted in the annulus first: one at the medial commissure, one at the lateral commissure, and one in the center of the posterior annulus. The slits on the valve chamber will align with the holes on the medial edge, lateral edge, and the center of the atrial flared portion of the crimped prosthetic valve respectively, such that the trailing DGF tails can easily be fed through the corresponding atrial flare holes, and then through the corresponding locking catheter in the valve housing, positioning, and locking system.

In one aspect, the VHPL system can be inserted into the patient's body and the DGF tails can be tensioned to guide the valve chamber, and thus the prosthetic valve, to the operative position at the previously implanted DGF head members. Once in position at the mitral annulus, the valve chamber sheath can be advanced to release the prosthetic valve starting with the atrial flared portion and continuing until the entire ventricular portion of the prosthetic valve has been released.

In one aspect, in order to gain better positioning of the heart valve leaflet replacement system, one or more sheaths within the MSML delivery system can be configured to be deflectable and/or steerable. Further in this aspect, it is contemplated that the heart valve leaflet replacement system can be implanted in the mitral annulus through a transfemoral, trans-septal procedure. As such, the docking sheath can be inserted into the femoral vein, advanced to the inferior vena cava and then can be articulated to bend the distal tip from the inferior vena cava through the trans-septal puncture site at the fossa ovalis to gain access to the left atrium. The VHPL system can be inserted through the docking sheath and advanced to the left atrium. The stent holder and valve chamber sheaths can be advanced, and the stent holder sheath can be articulated to bend the stent holder sheath tip towards the left ventricle and position the valve chamber in the center of the mitral annular orifice.

In one aspect, the prosthesis can be fixed in position at one or more implanted DGF head members prior to full release of the crimped prosthesis from the valve chamber by tensioning the respective DGF tail and engaging the corresponding DGF locking device with the prosthesis.

In one aspect, the VHPL system can be configured with a suture tensioning mechanism that can be operated to individually tension the DGF tails, or optionally a plurality of DGF tails simultaneously, to guide heart valve replacement system positioning and locking.

In one aspect, after valve deployment, the plurality of locking catheters can be advanced distally against the atrial flared portion of the stent while tensioning the DGF tails to engage the DGF locking mechanism with the prosthesis.

In one aspect, the locking catheters are configured to be flexible and can bend together with the other steerable sheaths during locking of the prosthesis. In another aspect, the distal tip of the locking catheters has a larger inner diameter than the DGF locking members such that they can pass over the DGF locking members. In this aspect, the locking catheters will be pushed against the atrial flared portion of the prosthesis until the DGF locking members are pulled through the atrial flare holes.

In one aspect, the lower ventricular portion of the stent can be configured with a mechanism to selectively engage the VHPL system such that the prosthesis can be guided, positioned, and fixed in place in a highly controlled manner. In one exemplary aspect, the stent holder can be configured with a recess with a complimentary shape to a tab on the lower ventricular portion of the stent frame, such that the tab fits inside the recess of the stent holder and the recess acts to hold the tab of the stent frame against the valve chamber inner wall until the valve chamber has been advanced distally enough to reveal the tab recess.

In one aspect, the lower ventricular portion of the stent frame can be configured with a tab on the tip of an extended member that is longer than the rest of the stent, such that, in operation, the tab is the lowest point of the stent. In one exemplary aspect, the stent frame can be configured similar to a stingray in shape where the extended member resembles the stingray tail that can be extended longer than the body of the stent frame, and the tip of the extended member can be configured to engage with the stent holder. In another aspect, the lower ventricular portion of the stent frame can be configured with a plurality of tabs or holes, or other engagement members on the tips of a plurality of extended members that are longer than the rest of the stent. The engagement members can be operatively engaged with complementary engagement members such as recesses or protrusions on the stent holder or the stent holder sheath.

In an optional aspect, the prosthesis can be released from the valve chamber leaving only the extended member tab engaged in the stent holder such that the prosthesis can expand fully in the mitral annulus. The locking catheters can be advanced and the DGF tails tensioned to lock the prosthesis in position at the implanted DGF members, while keeping the stent tab engaged in the stent holder. One skilled in the art will appreciate that, once the prosthesis is released, without a mechanism to hold the prosthesis in place, the blood pressure in the left ventricle can cause the prosthesis to migrate undesirably. By including a mechanism to restrain the prosthesis within the valve chamber until the prosthesis is fixed by the DGF locking members, the safety of the delivery and implantation process is greatly improved. This mechanism can be realized by a variety of different engagement members that can engage and disengage the prosthetic valve device with a portion of the VHPL system during the prosthetic valve deployment process.

In one aspect, it is contemplated that following deployment of the prosthetic valve and DGF locking members, should there be any paravalvular leak or instability of the valve in the operative position, a plurality of additional DGF members can be deployed on top of the prosthetic leaflet device with the DGF delivery system, such that each DGF head member of the additional DGF members is driven through the skirt material on the atrial flared portion of the prosthesis and embedded into the muscular annulus tissue until the body portion of the DGF body member lies flush against the atrial flared portion of the prosthesis. In this aspect, no additional fixation mechanism, i.e., locking member, is required on the DGF body member.

It is contemplated that following the implantation of the heart valve leaflet replacement system, all the components of the MSML delivery system can be removed, and a septal closing device can be inserted through the docking sheath to close up the hole on the atrial septum. Then the entire MSML delivery system can be removed from the body.

Various implementations described in the present disclosure can include additional systems, methods, features, and advantages, which can not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

A better understanding of the features and advantages of the present subject matter will be obtained by reference to the following detailed description that sets forth illustrative embodiments and the accompanying drawings. The features and components of the following figures are illustrated to emphasize the general principles of the present disclosure. Corresponding features and components throughout the figures can be designated by matching reference characters for the sake of consistency and clarity.

FIG. 1A illustrates the front view of the stent frame of the prosthetic valve, showing the atrial flared portion featuring a plurality of through-holes, and a lower ventricular portion featuring an elongated member with a tab. FIG. 1B illustrates the side view of the stent frame of the prosthetic valve. FIG. 1C illustrates the front view of the prosthetic valve, showing the three leaflets. FIG. 1D illustrates the side view of the leaflet attachment to the prosthetic valve stent, showing the prong structures of the middle leaflet attachment to the interior stent surface.

FIGS. 2A-2C show an exemplary aspect of a DGF member. FIG. 2A illustrates each component of the DGF member. FIG. 2B illustrates the top view of the DGF head member. FIG. 2C illustrates the DGF locking member and its components.

FIG. 3A is the side view showing the atrial flared portion of the stent being sandwiched between the DGF head and the DGF locking member. FIG. 3B illustrates the locations of the three DGF members along the flared portion of the prosthetic valve stent.

FIG. 8A shows the prosthetic valve (stent only for clear visual) is loaded into the valve chamber. FIG. 8B shows the release of the prosthetic valve by advancing the valve chamber distally. FIG. 8C shows the prosthetic valve stabilized during locking by a mechanism in the valve chamber, and the locking catheters being guided by DGF member tails (not shown) to the DGF members (not shown) on the prosthetic valve flared section, and locking the prosthetic valve in place. FIG. 8D shows that the prosthesis is fixed at the first three DGF members, and the entire valve housing, positioning, and locking system can be removed.

FIGS. 9A-9C are perspective views of an exemplary anchor delivery system. In this aspect, the anchor delivery catheter tip in FIG. 9A can be coupled to the end of the anchor delivery catheter shown in FIG. 9C. The inner wall of the anchor delivery catheter tip can be configured to have two pins for engaging and holding the anchor in place as shown in FIG. 9B. In this aspect, the tether can be looped through the through slot on the atrial side of the anchor.

FIG. 10 is a perspective view of the docking system consisting of a docking sheath with a compliant distal tip and a stiff proximal portion, and a docking handle including a tensioning mechanism.

DETAILED DESCRIPTION OF THE EXEMPLARY EMBODIMENTS

Figure 1A:
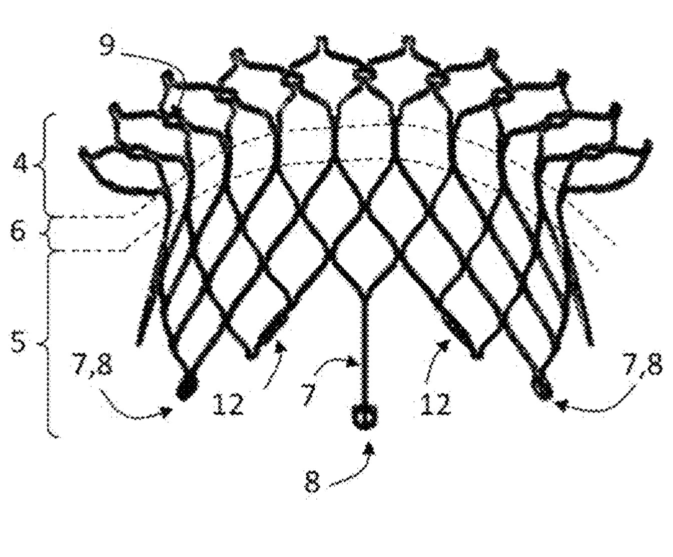
FIGS. 1A-1D illustrate different schematic views of the prosthetic valve.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description is provided as an enabling teaching of examples of devices, systems, and methods. To this end, those skilled in the relevant art will recognize and appreciate that many changes can be made to the various aspects described herein, while still obtaining the beneficial results of the present invention. It will also be apparent that some of the desired benefits of the embodiments herein invention can be obtained by selecting some of the features without utilizing other features.

Accordingly, those who work in the art will recognize that many modifications and adaptations are possible and can even be desirable in certain circumstances and are a part of the present invention. Thus, the following description is provided as illustrative of the principles of the present invention and not in limitation thereof.

For clarity, it will be appreciated that this disclosure will focus on the treatment of functional mitral regurgitation; however, it is contemplated that the heart valve leaflet replacement system and the associated methods can be used or otherwise configured to be used to treat other types of mitral regurgitation or to replace other diseased valves of the human heart, such as tricuspid valve, or could be used or otherwise configured to be used in other mammals suffering from valve deficiencies as well.

As used throughout, the singular forms "a," "an" and "the" include plural referents unless the context clearly dictates otherwise. Thus, for example, reference to "a leaflet" can include two or more such leaflets unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance can or cannot occur, and that the description includes instances where said event or circumstance occurs and instances where it does not.

The word "or" as used herein means any one member of a particular list and also includes any combination of members of that list. Further, one should note that conditional language, such as, among others, "can," "could," "might," or "may," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular embodiment.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these cannot be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems can be understood more readily by reference to the following detailed description of preferred embodiments.

Throughout the description, the terms "prosthetic valve" and "prosthesis" and "valve stent" and "heart valve leaflet replacement device" and "valve device" are used interchangeably and is contemplated as a heart valve replacement device described herein.

Throughout the description, the terms "distal" and "proximal" are expressed with reference to the operator during the use of the delivery system. "Distal" indicates an apparatus portion distant from, or a direction away from the operator and "proximal" indicates an apparatus portion near to, or a direction towards the operator.

One skilled in the art can appreciate the complexity of the transcatheter methods and systems used to successfully deploy a prosthetic valve into the heart. Such methods involve a number of components and a number of steps. Even though these components and steps are described in different parts of the description, it is understood that these components and steps do not necessarily need to be used and performed in such an order described herein in the description.

The heart valve replacement system described herein may be utilized with any heart valve replacement devices or prostheses. It is contemplated that the heart valve replacement system described herein comprises a series of systems that can be used concurrently to deliver a prosthetic valve 2 into a subject's heart.

In one aspect, the heart valve replacement system includes a multi-stage, multi-lumen (MSML) delivery system that can be configured to deliver the heart valve replacement device, or prosthesis 2, to the implanted site, or the native mitral annulus. Such system may include a dual-guiding-and-fixation (DGF) delivery system and a valve housing, positioning, and locking (VHPL) system. In one aspect, the DGF delivery system described herein is configured to implant a plurality of DGF members in the native annulus and to aid in guiding and fixing a prosthetic valve to the targeted implanted location. In one aspect, the novel VHPL system can be configured to house and organize a plurality of DGF member tails, crimped prosthetic valve, and can be designed to incrementally release a crimped prosthetic valve and to fix the prosthetic valve at the implanted DGF members via a DGF body fixation mechanism.

In one aspect, the MSML delivery system can access the mitral valve via the inferior vena cava, enters the right atrium, crosses the atrial septum to the left atrium then articulates downward to the native mitral annulus. It is contemplated that the MSML delivery system could also be navigated to the implantation site via the superior vena cava and follows the same previously described pathway towards the native mitral annulus.

Referring to FIGS. 1A-1D, in one aspect, a crescent shaped stent 3 of the MSML delivery system, can comprise an atrial flared portion 4, a ventricular portion 5, and a neck portion 6. In one aspect, the atrial flared portion 4, ventricular portion 5, and neck portion 6 are continuously attached to form a single body. At least a portion of the atrial flared portion 4 and/or a portion of the ventricular portion 5 can be formed to be self-expandable or balloon expandable to the desired operative position. In this aspect, it is contemplated that the stent 3 can be conventionally laser cut or woven into a desired shape that can be radially collapsible and expandable. Thus, it is further contemplated that the stent 3 can comprise a plurality of operatively linked components to form an expandable meshed or non-meshed body that can be made of a metal, or polymeric material, or biologically-made material, including but not limited to, cobalt chromium, stainless steel; or a metal having inherent shape memory properties, including but not limited to, Nitinol. Optionally, it is contemplated that the stent 3 can comprise a plurality of vertical stiff structures that are connected by compliant materials such as biological tissue, synthetic materials such as polymers and the like. The stent 3 can be configured to permit the natural dynamic motion of any remaining native leaflet(s) to coapt with prosthetic leaflet(s) 10.

In one aspect, when implanted, it is contemplated that the atrial flared portion 4 of the stent 3 can be configured to be positioned on and/or above the native annulus. In this aspect, the atrial flared portion 4 of the stent 3 can be configured to facilitate fixation and sealing of the prosthesis 2, which can assist in preventing paravalvular leakage and dislodgement post implantation. The mitral valve annulus is asymmetrical. The atrial flared portion 4 of the prosthesis 2 can be configured to cover or overlay the posterior portion of the mitral annulus, which is divided into three scallops, namely P1, P2 and P3. In one aspect, the atrial flared portion 41 can span the two commissures, i.e., the AC-anterior commissure and the PC-posterior commissure. In another aspect, the atrial flared portion 4 can comprise an anterior atrial flared portion as well as a posterior atrial flared portion, such that it covers the entire circumference of the mitral valve when operatively positioned.

Figure 1B:
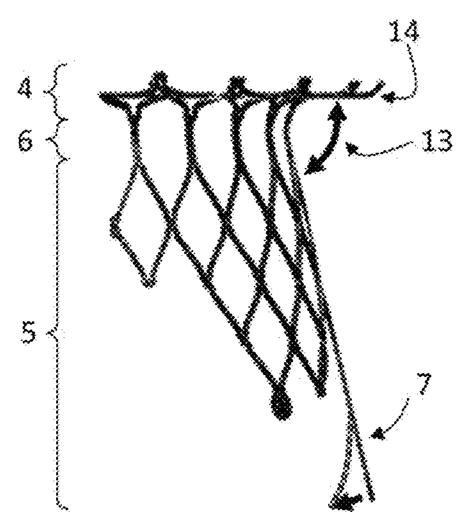

In one aspect, as depicted in FIGS. 1A-1B, at least a portion of the atrial flared portion 4 has a bend 14. In this aspect, the bend can be an upward curl away from the heart chamber wall to prevent over expansion of the heart chamber that could result in deep penetration of the heart tissue. In a further aspect, the upward curl portion is oriented between about ninety and one hundred twenty degrees (90-120°) from the atrial flared portion 4. In a further aspect, this bend 14 is only at the cell struts of the atrial flared portion 4, thus, does not interfere or distort the circular shape of the through-holes 9 in the atrial flared portion 4.

In another aspect, at least a portion of the atrial flared portion 4 is configured to have a plurality of through-holes 9 to selectively engage the DGF members 101. In one aspect, the through-holes 9 can be designed with a circular shape, connecting the cell struts and forming a bridge connection with the neighboring cells. The through-holes 9 can be designed at every bridge connection of the atrial flared portion 4. In another aspect, the through-holes 9 can be designed at fewer locations than the total number of bridge connections of the atrial flared portion 4.

In one aspect, the entire circumference of the ventricular portion 5 of the stent can be bent towards the left ventricle wall. Referring to FIG. 1B, the bending angle 15 can be between sixty and one hundred twenty degrees (60-120°) with respect to the atrial flared portion 4 of the stent 3.

Referring to FIGS. 1A and 1B, in one aspect, the stent 3 is configured with an extending member 7. In one aspect, the extending member 7 can be configured as a straight segment. In another aspect, the extending member 7 can be configured with a short extension length and a tab 8 at a distal end that is continuously connected to the straight segment.

In one aspect, the tab 8 can be configured to have a larger width than the rest of the extending member 7.

In an exemplary aspect, at least one extending member 7 can be designed at the center of the distal portion of the ventricular portion 5 of stent. In this aspect, in the operative position, the extending member 7 is the longest section of the stent 3 that extends the furthest into the left ventricle. In this aspect, the extending member 7 is about two to seven millimeters (2-7 mm) longer than the other parts of the stent 3.

In an exemplary aspect, and as depicted in FIG. 1B, the extending member 7 can be configured to curve inward radially to avoid interference with the posterior wall of the ventricle in operation.

In an optional aspect, the extending member 7 can be located at other sections along the circumference of the ventricular portion 5 of the stent. In an exemplary aspect, referring to FIG. 1A, the extending member 7 can extend from one or more lower cells of the ventricular portion 5 of the stent 3.

Referring to FIG. 1A, in one aspect, the tab 8 of the extending member 7 is configured to hold the prosthesis during release from the VHPL system to prevent it from migrating unexpectedly before the DGF fixation mechanism can be engaged. In this aspect, the (VHPL) system 1 is selectively designed to attach to the tab 8 of the extending member 7 until the prosthesis is secured to the targeted implanted location. Once the prosthesis 2 is fully fixed in the implanted position, the tab 8 could be selectively released from the (VHPL) system 1 to disengage the prosthesis 2 from the (VHPL) system 1.

In one aspect, the tab 8 is configured with a dome, circular, square, rectangular, triangular, or irregular shape. In another aspect, the tab 8 is configured with at least one-through hole.

Figure 1C:
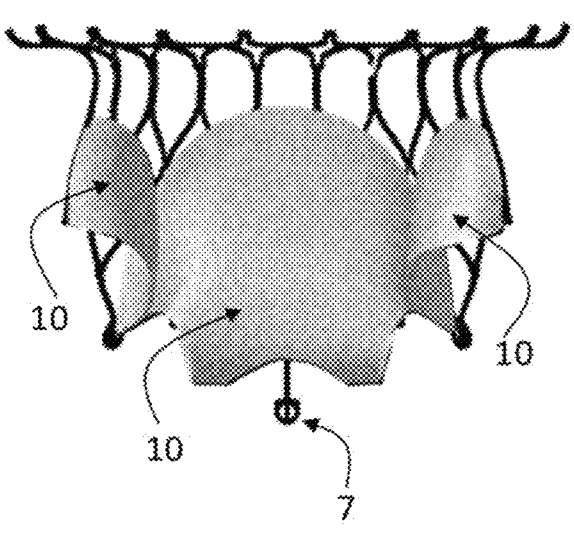
Figure 1D:
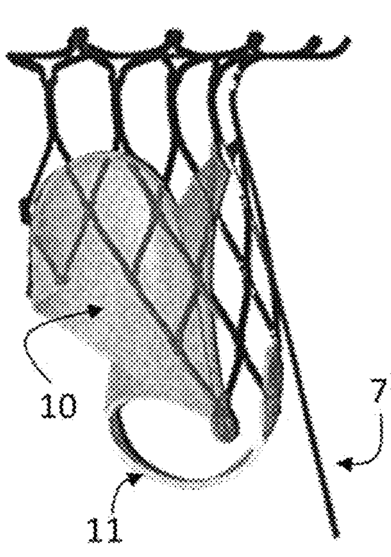

In one aspect, at least one prosthetic leaflet 10 is mounted on an inner surface of the ventricular portion 5 of the stent 3, as depicted in FIGS. 1C and 1D. In a further aspect, at least one prosthetic leaflet 10 of the plurality of prosthetic leaflets has a different shape. In another aspect, at least one prong structure 11 of the at least one prosthetic leaflet 10 comprises a plurality of prong structures 11. It is contemplated that at least one prong structure 11 is coupled to the leaflet free edge.

In one aspect of the MSML delivery system, the prosthetic leaflets 10 can be configured similarly in shape to the native posterior mitral leaflets.

It is contemplated that the at least one prosthetic leaflet 10 and at least one prong structure 11 can be configured with one single, flat piece of flexible material such as biological tissue, polymeric material, or fabric, and can be attached to the stent 3 in such a way that it creates a 3D dome-like structure billowing radially inwards from the stent attachment points. The prosthetic leaflet 10 can be configured to be mobile during the cardiac cycle, where the prosthetic leaflet 10 moves closer to the inner surface of the stent during diastole, and further away from the inner surface of the stent in systole.

Referring to FIG. 1C, in one aspect, the at least one prosthetic leaflet 10 can comprise three leaflets: two smaller lateral leaflets, and one large central leaflet, which form three distinct dome-like structures extending radially from the inner surface of the ventricular portion 5 of the stent 3. In this aspect, the three leaflets can be configured to span the circumference of the lower ventricular portion of the stent. The prosthetic leaflets 10 can be mounted closely together on the inner surface of the stent 3 in order to prevent transvalvular leakage in operation. Further, in this aspect, the leaflets can be configured to billow inward radially from the stent 3 such that they are positioned in the blood flow track in operation and can close the mitral orifice under systolic blood pressure.

In one exemplary aspect, as shown in FIGS. 1C-1D, the smaller lateral leaflets can be asymmetric with a shorter length on the lateral edges corresponding to the shape of the lower ventricular portion 5 of the stent 3. In one aspect, the larger central leaflet can have a symmetric shape and two prong structures 11 extending from the leaflet free edge. Further, in this aspect, the free ends of the prongs 11 can attach to portions of the stent 3, for instance, by sewing the ends of the prongs 11 to the stent via the through-holes 12 in the lower ventricular portion 5 of the stent 3. In this aspect, the prong structures 11 prevent excessive billowing and prolapse of the large central leaflet and also help to evenly distribute stress in the prosthetic leaflet 10 which is important for durability. Optionally, one or more prong structures 11 can be added to the lateral leaflets.

Figure 5:
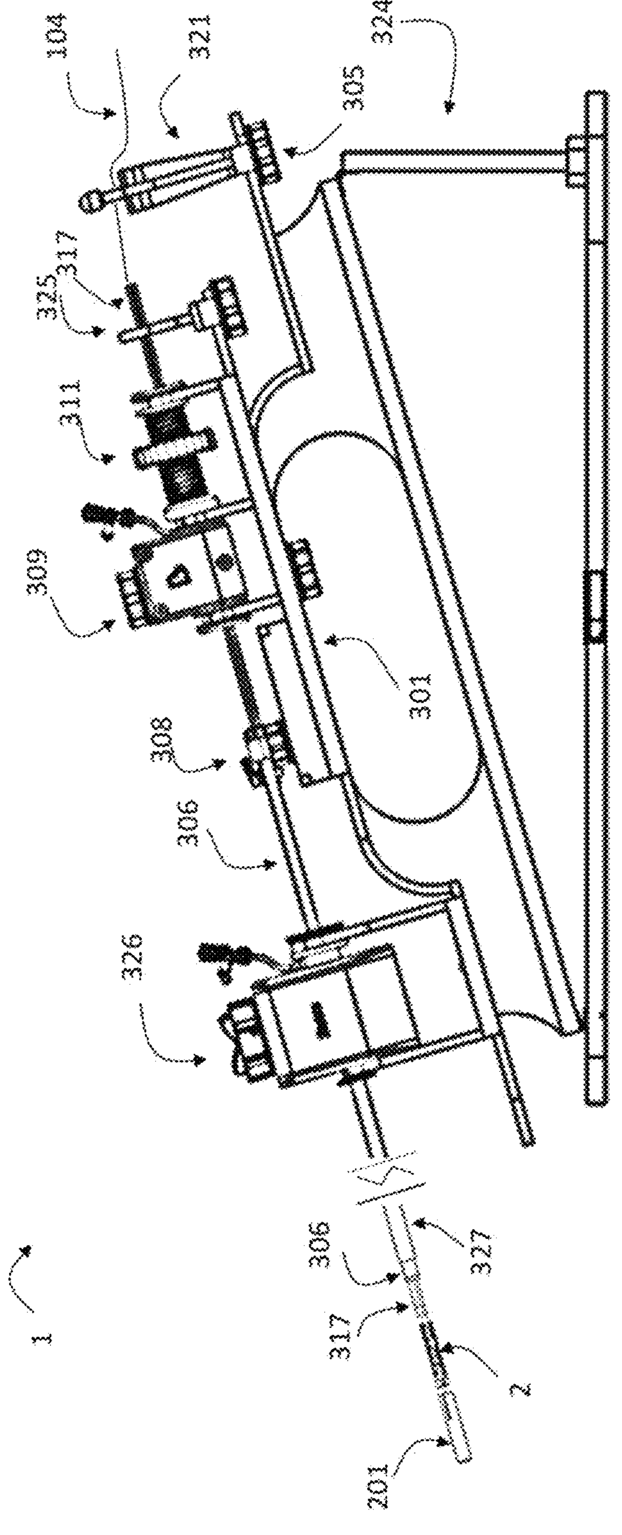
FIG. 5 is a schematic of a docking system and valve housing, positioning, and locking system mounted on an angled base.

Referring to FIG. 5, the MSML delivery and implantation system can comprise a docking system 326, a DGF member delivery system, and a VHPL system 1, which can be mounted on a handle platform 301 to facilitate the delivery process. The handle platform 301 is mounted on a base 324.

In one aspect, the base 324 features a mechanism that allows for adjustment of the angle of the MSML system to optimally enter the access site of the body. The base 324 can be made of, but is not limited to, rigid materials such as metals, plastics, and others of the like.

In one aspect, the docking system 326 includes a docking sheath 327 and a docking handle. The docking sheath 327 may first enter the body through an introducer sheath. In one exemplary aspect, the docking sheath 327 can be configured to be deflectable in order to access the implantation site. In this aspect, the distal end of the docking sheath 327 can be configured to bend up to one hundred eighty degrees (180°) with respect to the proximal end of the sheath.

Once the docking system 326 is in place, the DGF system can be introduced. In this aspect, a plurality of DGF members 101, e.g., as shown in FIG. 2, can be sequentially or simultaneously delivered and implanted at the desired locations on the annulus.

In a further aspect, it is contemplated that a method of implanting DGF members 101 can be implemented prior to the delivery of the prosthesis 2.

Referring to FIG. 2A, in one aspect, the DGF member 101 can comprise a DGF head member 102, a DGF body member 103, a DGF locking member 105, and a tether 114, which are intended to be permanently implanted in the mitral annulus.

In another aspect, implanting additional DGF members 101A can be implemented after the delivery and fixation of the prosthesis 2. In this aspect, the DGF members 101A can be configured with a DGF head member 102, a DGF body member 103 and a DGF tether 114 forming a loop.

In one aspect, as shown in FIG. 2B, the DGF member 101 is configured with a head portion 102 which engages the tissue on or around the annulus, and a body portion 103 with an engager 109 that engages a DGF delivery catheter, such as catheter 48 shown in FIGS. 9A-9C.

It is further contemplated that the DGF head member 102 can be configured to implant into the native annulus tissue and to resist separation after implantation. In an exemplary aspect, the DGF head member 102 can have, but is not limited to, a spiral shape, a coil shape, a pronged shape, a screw shape, and a barbed hook shape that engages the annular tissues. The DGF head member 102 can be formed of, but is not limited to, Nitinol, stainless steel, cobalt chromium, polymer, and the like.

In one exemplary aspect, the DGF head member 102 is configured with a coil 108 with a length between about four and ten millimeters (4-10 mm), and a diameter between about two and five millimeters (2-5 mm), formed with wire with a diameter between 0.25 and one millimeter (0.25-1.0 mm).

In one aspect, the DGF head member 102 can be configured with a stabilization member 111 to facilitate controlled implantation of the DGF head member 102 into the annular tissue via the DGF delivery system in operation. In one exemplary aspect, the stabilization member 111 is configured as a straight wire with a diameter between about 0.25 and one millimeter (0.25-1.0 mm) extending axially through the center of the spiral with a sharpened tip extending between about one and three millimeters (1-3 mm) beyond the end of the spiral. In a further aspect, the stabilization member 111 could be configured as a needle with a sharpened distal tip 112 that extends axially beyond the DGF head member coil 108 by about one to five millimeters (1-5 mm). In operation, the stabilization member 111 can be used to engage the annular tissue prior to screwing in the DGF head member 102 into the tissue, which will help to prevent undesired motion of the DGF delivery system, so the DGF head member 102 can be easily implanted at the desired position along the annulus. It can be appreciated that such stabilization member 111 can be used to engage the tissue with the DGF member at the preferable implantation site and prevent the DGF member from moving from the target location during implantation.

In a further aspect, the tip 119 of the coil 108 of the DGF head member 102, as exemplified in FIG. 2A, can be shaped and configured to facilitate easy penetration into the annular tissue. In one exemplary aspect, the tip 119 of the coil 108 is sharpened and curved to the same pitch as the remainder of the coil 108. In another exemplary aspect, the tip 119 can be straight. In another optional aspect, the tip 119 can have an arc length between about one and three millimeters (1-3 mm).

In another aspect, as shown in FIG. 2B, the DGF body member 103 comprises a base and an extruded section 109 that is configured for engaging the DGF delivery catheter 48 shown in FIGS. 9A-9C. In this aspect, the base and the extruded section can be one piece. In a further aspect, the extruded section 109 has a smaller dimension than the outer diameter of the base so that the DGF delivery catheter 48 can engage it.

In one aspect, the extruded section 109 comprises three through holes, with two of the holes 110 configured for attachment of the DGF locking member 105 via the tether 114. In this aspect, the distal section of the tether 114 is fixed to the DGF body via the two attachment holes 110, the middle portion of the tether 114 is configured to loop through the DGF locking member 105 in such a way that constrains the DGF locking member 105 from moving along the tether 114, and the proximal section of the tether 114 at the proximal side of the DGF locking member 105 is configured with a loop.

In one aspect, the DGF body member 103 comprising the DGF locking member is configured for attaching a DGF tail member 104 via the loop at the proximal side of the tether 114.

In one aspect, the tether 114 can be straight, curved, single, or double or multiple lines.

In one aspect, the distance between the DGF body member 103 and the DGF locking member 105 can be between about 0.4 and one millimeter (0.4-1.0 mm) such that the atrial flared portion 4 of the stent 3 can fit snugly between DGF body member 103 and the DGF locking member 105 in the operative position. Optionally, each DGF body member 103 can include a plurality of DGF locking members 105, where the spacing between adjacent DGF locking members 105 can be between about 0.4 and two millimeters (0.4-2.0 mm). The DGF body member 103 and DGF locking members 105 can be separated on the tether 114 by, for example, tying a plurality of knots on the tether 114. In a further aspect, if the tether 114 is made of metal or plastic of the like, small protrusions can be welded, molded, or adhered to the flexible component to maintain the spacing.

In one aspect, it is contemplated that the tether 114 containing the DGF locking member 105 can be formed of a tether made from suture, string, wire, or polymeric material.

Referring to FIG. 2A, it is contemplated that the DGF head member 103 and DGF body member 103 can be formed as a single component or optionally, by joining distinct parts by one or more of welding, bonding, adhesives, and the like that can resist separation during in vivo loading. Further, in this aspect, the DGF head member 103 and DGF body member 103 may be formed with strong and biocompatible materials such that they can be permanently implanted in the human body and resist damage, for example, but not limited to, stainless steel, cobalt chromium, nitinol, non-absorbable polymer, biological material and the like.

In one exemplary aspect, it is contemplated that the DGF locking members 105 can be configured to allow passage of a portion of the atrial flared portion 4 of the stent 3, guided by the DGF tail member 104, in one direction only, and to resist the subsequent movement of the atrial flared portion 4 of the stent 3 in the opposite direction.

In one aspect, the DGF locking member 105 can be configured such that it can selectively be compressed to a diameter smaller than the diameter of the through-hole 9 on the atrial flared portion 4 of the stent 3, such that it can pass through the hole, and subsequently be selectively re-expanded to its original size, larger than the diameter of the through-hole 9 to prevent backward motion of the DGF locking member 105 through the hole.

In one exemplary aspect, referring to FIG. 2C, the DGF locking member 105 can be configured with proximal 107 and distal 106 portions. In one aspect, the locking member 105 can have a total length between about 1.5 and 3.5 millimeters. The length of the proximal portion 107 can be between about 0.5 and 1.5 millimeters. The length of the distal portion 106 can be between about one and two millimeters (1.0-2.0 mm).

In one aspect, the proximal portion 106 comprises a tubular shape with an outer diameter ranging between about 0.5 and 1.5 millimeters and an inner diameter ranging between about 0.4 and 1.2 millimeters. In one aspect, the distal portion 106 of the DGF member 101 comprises a plurality of radially compressible legs forming a cone shape in its original state. In one aspect, the outer diameter of the proximal portion of the locking member is smaller than the inner diameter of the through-hole 9 on the atrial flare 4 of the stent 3. Further, in this aspect, the distal tip 107 of the DGF locking member 105 can be configured with a maximum fully-expanded outer diameter that is larger than the inner diameter of the through-hole 9 on the atrial flare 4 of the stent 3 such that it cannot pass through the through-hole 9. The proximal 107 and distal 106 portions of the DGF locking member 105 can be connected and continuous.

In operation, the DGF member tails 104 can be tensioned to pull the proximal portion 107 of the DGF locking member 105 into the through-holes 9, and as the distal portion 106 of the DGF locking member comes into contact with the edges of the through-hole 9, it will collapse radially, such that its outer diameter is less than the inner diameter of the through-hole 9, which will allow the DGF locking member 105 to pass through the through-holes 9. Once the DGF locking member 105 has completely passed through the through-holes 9, the DGF distal portion 106 can re-expand to its original size to prevent backward motion of the DGF locking member 105 through the through-holes 9.

It is contemplated that the DGF locking member 105 can be manufactured, for example, by laser cutting a plurality of slits from a tube, then deforming the legs by bending these legs outwards radially. In exemplary embodiments, the slit may be between about 0.3 to 0.6 millimeters wide and between about 0.6 to 1.5 millimeters long. A heat-treatment process can be done to form the final flared cone shape geometry. The legs are designed so that they can be selectively compressed to pass through the through-holes 9, and then re-expand and return to their original shape once fully passed through the through-holes 9.

In one aspect, it is contemplated that the one or more DGF locking members 105 can be formed of, but are not limited to polymers, polytetrafluoroethylene (PTFE), stainless steel, Nitinol, and metal-like materials, or a combination of these materials.

In one aspect the extruded section 109 of the DGF body member 103 can be configured as a protrusion which is shaped to fit snugly in a complimentary recess within the distal tip of the DGF delivery catheter 48, such that, when the protrusion is engaged with the distal DGF delivery catheter 48, rotation of the DGF delivery catheter 48 in one direction will engage the DGF head member 102 with the tissue and rotation of the DGF delivery catheter 48 in another direction will result in disengaging the DGF head member 102 from the tissue.

In an exemplary aspect, the extruded section 109 of the DGF body member 103, as shown in FIG. 2B, can have a rounded rectangular shape which is raised about 0.5 to two millimeters (0.5-2 mm) from the base of the DGF body member 103.

In one aspect, as shown in FIG. 2A, the loop on the tether 114 can be configured to engage the DGF tail member 104. In one exemplary aspect, one end of the DGF member tail 104 can be inserted through the loop on the tether 114, and both free ends of the DGF member tail 104 can extend through and out of the proximal side of the MSML delivery system.

In one aspect, the DGF member tail 104 links the DGF delivery system and the VHPL system 1. In this aspect, the DGF member tail 104 acts as a bridging element to guide the VHPL system 1 from the access site to the implantation site.

In one aspect, it is contemplated that after DGF member 101 deployment, the two free ends of the DGF member tails 104 can be inserted through the atrial flared through-holes 9 of the prosthesis 2. As such, both free ends of the DGF member tails 104 can also be inserted into the VHPL system 1, such that when an operator pulls on the exiting free ends of the DGF member tails 104 away from the body, the DGF member tails 104 can be tensioned and guide the VHPL system components towards the DGF members 101 implanted in the annulus. Further tensioning of the DGF tail members 104 will aid in fixing the prosthesis to the annulus via the DGF locking members 105 on the DGF member 101. Following device implantation, DGF member tails 104 can be removed from the VHPL system and from the body by pulling one free end of DGF member tails 104.

In another aspect, one end of the DGF tail members 104 can be tied to the loop and the other end can extend out of the body to the proximal side of the MSML delivery system. In this aspect, once the heart valve leaflet replacement device is implanted and fixed in position, the trailing DGF tails can be cut by traditional cutting methods or a trans-catheter suture cutting device.

It is contemplated that the DGF tail member 104 can be configured to fit within the inner catheters of the MSML delivery system and be long enough to extend from the DGF body member 103 and exit the MSML delivery system. In this aspect, the DGF tail member 104 can have a diameter of about 0.1 to 0.5 millimeters and can be at least about 2.5 meters in length.

Figure 3A:
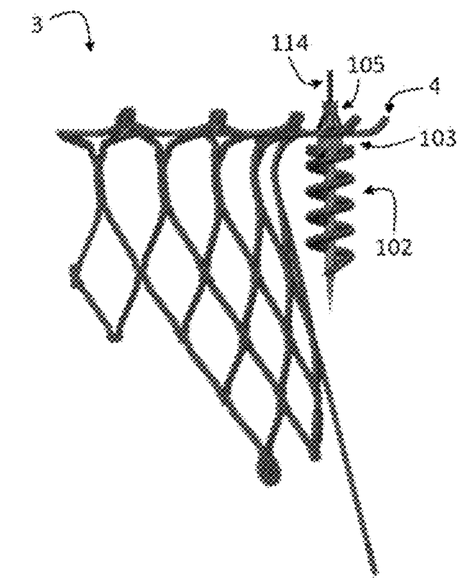
FIGS. 3A and 3B are schematic views of the stent fixed in position by a plurality of DGF members.

Referring to FIG. 3A, in one aspect, after prosthesis 2 implantation, the atrial flared portion 4 of the prosthesis 2 will be sandwiched between the DGF locking member 105 and the DGF body member 103. It can be appreciated that the spacing between the DGF locking member 105 and the DGF body member 103 is optimized so that there is limited motion of the prosthesis 2 after implantation.

Figure 3B:
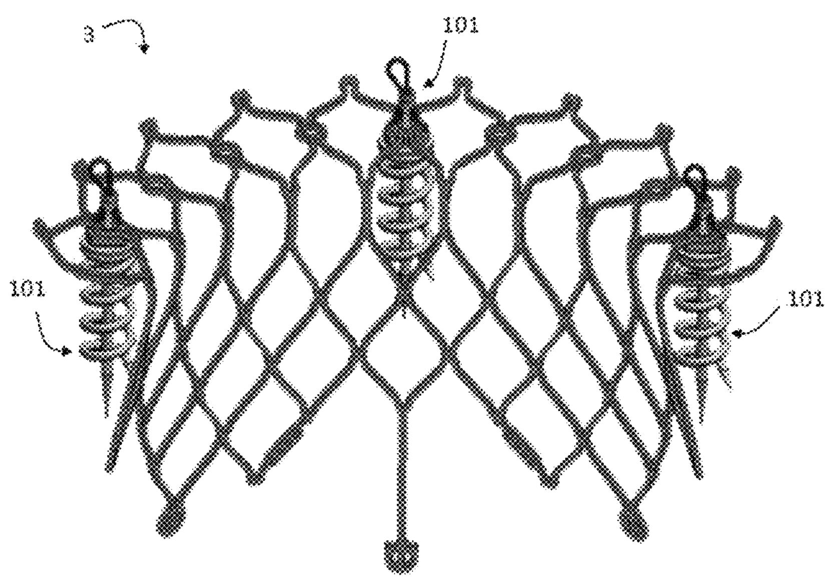

Referring to FIG. 3B, in one aspect, at least three DGF members 101 are implanted, with two DGF members 101 implanted at the lateral portions and one at the center of the atrial flared portion 4 of the stent 3.

Figure 4:
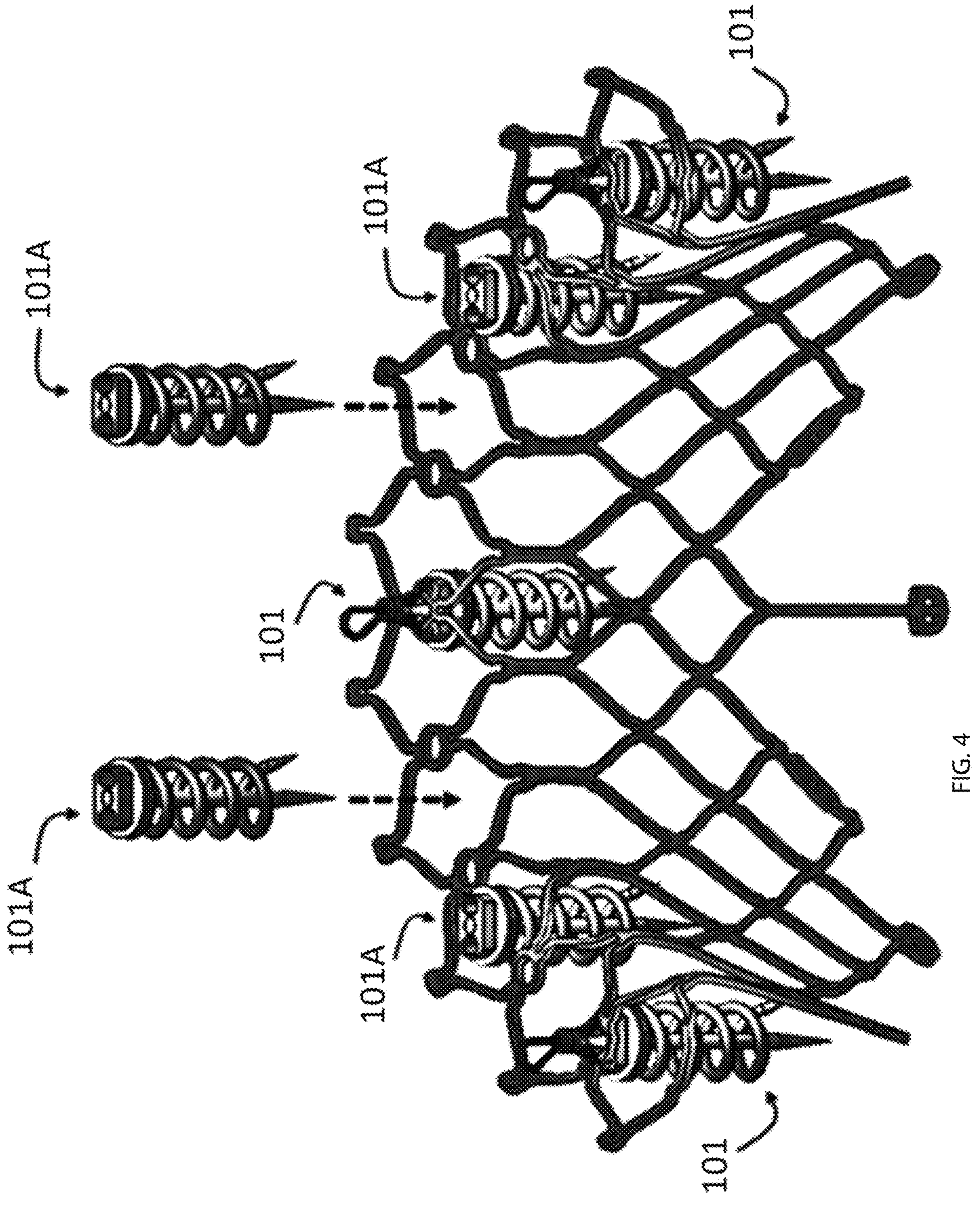
FIG. 4 is a schematic view depicting one aspect where additional DGF members without the DGF locking members are implanted in the atrial flared portion of the stent.

In one aspect of the method of using the MSML delivery system, at least three DGF members 101 are implanted in the annulus prior to the implantation of the prosthesis 2 via the VHPL system 1. Once the prosthesis 2 is implanted, at least one additional DGF member 101A—without the DGF locking member 105—will be implanted over the atrial flared portion 4 of the prosthesis 2. The DGF members 101A can penetrate the skirt material of the prosthesis and anchor into the tissue. In another aspect, the DGF members 101A can be configured to go through the through-hole 9 of the atrial flared portion 4. Referring to FIG. 4, as illustrated, three DGF members 101 can be implanted at the lateral sides (P1 and P3) of the atrial flared portion 4, one DGF member 101 can be implanted at the center (P2) of the atrial flared portion 4. Additional DGF members 101A can be implanted between the DGF members 101 at P1 and P2, as well as P2 and P3 locations. By implanting additional DGF members 101A, as one skilled in the art will appreciate, paravalvular leakage between the prosthesis 2 and the annulus can be eliminated, and dislodgement of the prosthesis 2 can be prevented, thus allowing normal coaptation between the prosthetic leaflets and the native leaflet.

For clarification, the following description outlines one exemplary VHPL system 1 design for successfully delivering and fixing the prosthesis. The shape and designs of the outer compartments, constructions and assembly of the VHPL system 1 controls may change as long as they can perform the same general functions, i.e., translation or restricted motion of a sheath, tensioning of a wire or tether, etc. Thus, the illustrations displayed herein are for a better description and clarification but not limited to a specific design of any components.

Figure 6:
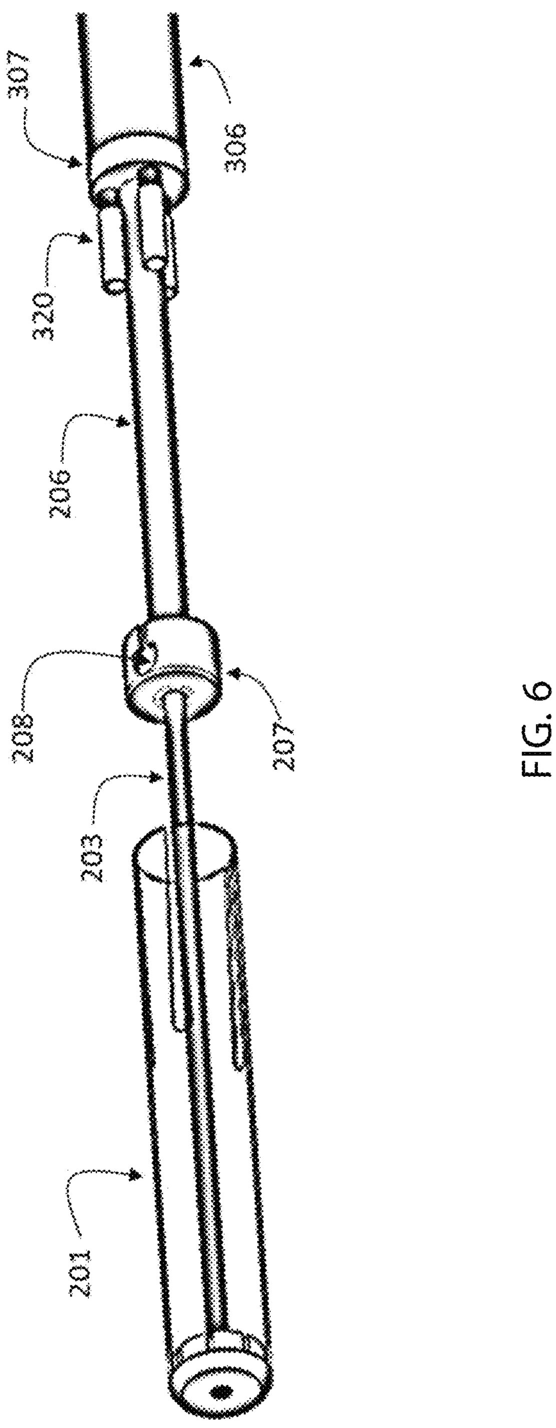
FIG. 6 is a schematic of the valve housing, positioning, and locking system catheters with the valve chamber attached to the distal section, follow by the stent holder mounted on the steerable stent holder sheath, and a plurality of locking catheters; all reside within the guide sheath and separated by a separator.

Referring to FIG. 6, in one aspect, the VHPL system 1 can comprise an outer sheath 306 that houses a plurality of catheters and tubes that function to deliver a prosthesis.

In one aspect, the outer sheath 306 can be a guide sheath. In this aspect, the guide sheath 306 may house a stent holder sheath 206 that is attached to a valve chamber, 201 which houses a prosthetic valve in a crimped stage. In this aspect, the stent holder sheath 206 can deflect to guide and position the valve chamber 201 from the access site to the left ventricle. In this aspect, the valve chamber 201 is connected to a valve chamber sheath 203 that can slide along the inner lumen of the stent holder sheath 206. In this aspect, the sliding of the valve chamber sheath 203 is the mechanism to release the prosthetic valve.

In one aspect, the outer sheath 306 may house a plurality of locking catheters 317. In this aspect, the locking catheters 317 and the stent holder sheath 206 can be organized with a multi-lumen guide sheath 306, all of which can be inserted into the body through a larger diameter docking sheath 327. In operation, the prosthetic valve 2 is guided to a plurality of previously implanted DGF members 101 by tracking over the DGF tails 104, which are loaded through the atrial flare holes 9 of the crimped prosthetic valve 2 and through the corresponding locking catheters 317 to the proximal end of the VHPL system 1.

In this aspect, the valve chamber sheath 203, stent holder sheath 206, locking catheters 317, and guide sheath 306 are configured to move independently of the docking sheath 327 to gain proper positioning. Further, the valve chamber sheath 203 and stent holder sheath 206 are configured to move together and independently of the locking catheters 317 and guide sheath 306. To deploy the valve 2, the valve chamber sheath 203 can be advanced relative to the stent holder sheath 206. To fix the prosthesis 2 in place, the DGF member tails 104 must be tensioned individually while each locking catheter 317 is individually advanced. Once the prosthesis 2 is fully released and fixed in place, all the sheaths can be retracted together, out of the patient's body.

One skilled in the art can appreciate the need for a precise and stable valve release mechanism. Thus, the VHPL system can be mounted on a handle platform 301, e.g., as shown in FIG. 5. In the example shown, the handle platform 301 sits proximal to the docking system 326 on base 324. The outermost guide sheath 306 and the associated inner sheaths, on the handle platform 301, are inserted into the docking sheath 327. The handle platform 301 is configured such that it allows the guide sheath 306, the stent holder sheath 206, and valve chamber sheath 203 to slide simultaneously along the base 324 at specified distances. In a further aspect, the handle platform 301 is designed to prevent rotation of the guide sheath 306 throughout the valve delivery process. The handle platform 301 can be made of any rigid and durable material, such as metals, plastics, and the like.

In one aspect, the guide sheath 306 is composed of a distal and proximal portion.

In one aspect, the distal portion of the guide sheath 306 may be made of a composition of materials that are flexible and conforms to the sharp curvature of the deployment pathway in the native heart chambers, one of which including from the inferior vena cava to the septum; and the proximal portion of the guide sheath 306 may be made of a composition of materials that are more rigid than the distal portion for the purpose of preventing buckling during the delivery process.

In one aspect, the distal end of the guide sheath 306 can be configured with a separator 307. In this aspect, the separator 307 of the guide sheath 306 acts as an organizer to separate the internal sheaths within the guide sheath 306 to avoid tangling throughout the prosthetic valve delivery process.

In one aspect, the separator 307 of the guide sheath 306 is a separate component that is fixed to the distal portion of the guide sheath 306. In one aspect, the separator 307 may be a cylinder component that has at a plurality of lumen. In one aspect, the separator 307 can have multiple lumens, e.g., four lumens, with one center lumen and three outer lumens surrounding the center lumen. In this aspect, the center lumen that houses the deflectable stent holder sheath 206 and the three peripheral lumens that house the locking catheters 317. As one can appreciate, the separator 307 organizes the internal sheaths within the guide sheath 306 to avoid tangling throughout the prosthetic valve 2 delivery process.

In another optional aspect, the guide sheath 306 can be configured as a multi-lumen tube throughout its entire length with no additional separator 307. In this aspect, the multi-lumen guide sheath can have four lumens, one in the center and three in the peripheral, and all lumens are separated by the walls.

In one aspect, the stent holder sheath 206 can deflect and translate along the handle platform. In this aspect, the stent holder sheath 206 can be mounted on a handle system 309, 301 that allows the operator to deflect the distal portion of the stent holder sheath 206. In further aspect, the stent holder sheath 206 can be mounted on a handle system that can slide.

Referring to FIG. 6, in one aspect, the deflectable stent holder sheath 206 can be at the center lumen of the guide sheath separator 307. In one aspect, the deflectable stent holder sheath 206 can be configured as a composite sheath comprising portions of varying stiffness and flexibility, among other notable characteristics such as pushability and kink-resistance. These characteristics allow the stent holder sheath 206 to deflect from 0° to 180° while maintaining its integrity and ability to deflect the sheathes contained within.

In one aspect, deflectable stent holder sheath 206 can comprise three sections, i.e., the distal, middle and proximal sections. In this aspect, the distal section is a stiff straight section in which the prosthetic valve 2 is crimped over. The middle section of the deflectable stent holder sheath 206 is a soft, coiled section that has an inherent ability to bend in a tight radius without kinking or causing damage to any sheaths residing within. The proximal portion of the deflectable stent holder sheath 206 is a long stiff section that provides stability and rigidity that spans throughout the VHPL 1. At least one pull wire is embedded within the walls of the deflectable stent holder sheath 206. By selectively tensioning the at least one pull wire, the deflection of the soft middle section can be controlled.

In this aspect, the stent holder 207 functions as a safety feature within the delivery system to maintain control and repositionability of the prosthetic valve before it is fully deployed and locked onto the native mitral annulus. The tab 8 on the extending member 7 of the stent 3 is released from the stent holder 207 when the valve chamber 201 is translated distally past the stent holder 207, thereby completely freeing the prosthetic valve from the valve chamber 201.

In one aspect, the distal section of the VHPL system 1 can comprise a valve chamber 201 to house the prosthetic valve 2 within the VHPL system 1. In this aspect, the prosthetic valve 2 can be crimped down to fit within a valve chamber 201 on the distal end of the VHPL 1, and subsequently be selectively expanded to an operative size and positioned once released from the valve chamber 201.

Figure 7:
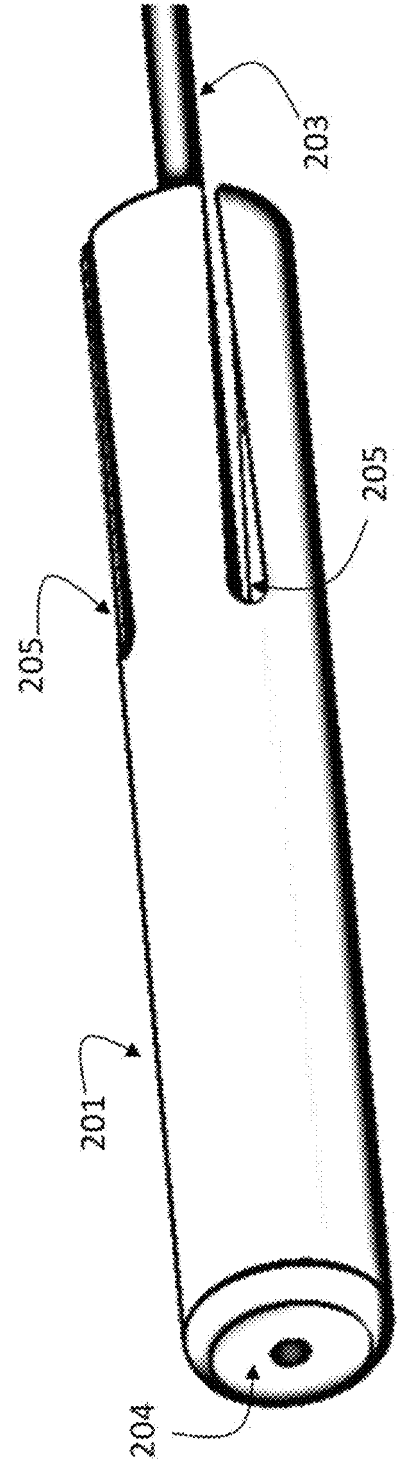
FIG. 7 is a perspective view of the valve chamber attached to the distal end of the valve chamber sheath.
Figures 8A, 8B, 8C, 8D:
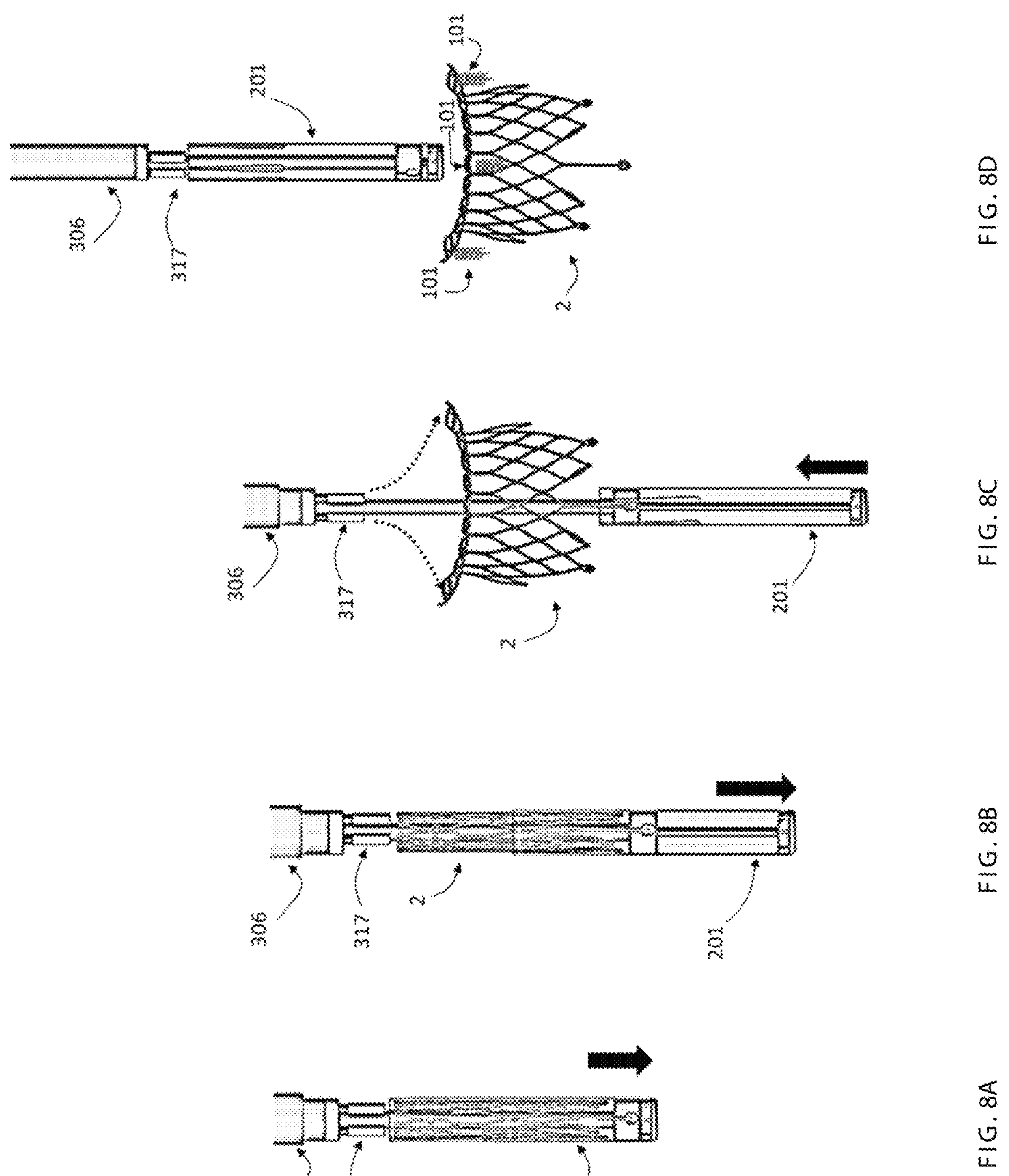
FIGS. 8A-8D illustrate a heart valve leaflet replacement system and steps for loading, releasing, and locking a prosthetic valve.

In one aspect, referring to FIG. 7, the valve chamber 201 can include a cylinder or conical shape, which is closed on the distal end and has an inner diameter of about six to eight millimeters (6-8 mm), or large enough to house the crimped prosthetic valve 2, and an outer diameter of about seven to nine millimeters (7-9 mm) or small enough to fit within the docking sheath. The length of the valve chamber lumen can be configured to be larger than the length of the crimped prosthetic valve 2, such that it can house the entire crimped prosthetic valve 2 inside. The length of the valve chamber lumen can be about twenty to fifty millimeters (20-50 mm).

In a further aspect, a smaller diameter valve chamber sheath 203 can be configured to attach to the closed end on the distal end of the valve chamber 201 which extends to the proximal side of the VHPL system 1, such that the valve chamber 201, and thus the prosthetic valve 3, position within the heart can be controlled by manipulating the valve chamber sheath 203 on the proximal side, i.e., the operator's side, of the VHPL system 1.

It is contemplated that the distal end of the valve chamber 204 and the cylindrical part of the valve chamber 201 can be made from one solid piece of material or optionally from separate pieces and of similar or dissimilar materials that are otherwise attached together. Referring to FIG. 6, in an optional aspect, the distal end of the valve chamber 201 can be configured with a central lumen to facilitate attachment to the valve chamber sheath 203 and rounded edges to prevent damage to surrounding tissues in operation.

The valve chamber sheath 203 can be optionally configured as a tube or solid rod. In one aspect, the valve chamber sheath 203 can be configured with multiple sections with varied stiffness along its length. Ideally, the valve chamber sheath 203 can be configured with a stiff distal section within the valve chamber 201, followed by a compliant middle section to allow for bending and facilitate maneuvering of the VHPL system 1 within the patient's body, followed by another stiff section at the proximal end to provide pushability.

In one aspect, a stent holder 207 can be configured to fit within the lumen of the valve chamber 201 with the same outer diameter as the crimped prosthesis 2. The stent holder 207 can be configured to attach to the distal tip of a smaller diameter stent holder sheath 206 that extends to the proximal side of the VHPL system 1, such that the stent holder 207 position within the valve chamber 201 can be controlled by manipulating the stent holder sheath 206 on the proximal side of the VHPL system 1.

In one aspect, in operation, the stent holder 207 can be positioned distal to the crimped prosthesis 2 within the valve chamber 201. Thus, the valve chamber lumen can be configured with a length that is longer than the lengths of the stent holder 207 and crimped prosthesis 2 added together.

It is contemplated that the prosthetic valve 2 can be crimped over (around) the stent holder sheath 206 proximal to the stent holder 207 and loaded into the valve chamber 201. The valve stent 2 can then be subsequently released from the valve chamber 201 by advancing the valve chamber sheath 203 distally with respect to the stent holder 207. The stent holder 207 will prevent distal motion of the prosthesis 2, and as the valve chamber 201 is moved distally, the prosthesis 2 will be released from the valve chamber 201 beginning with the proximal side of the valve stent 2 and ending with the distal side of the prosthesis 2.

In one aspect, referring to FIG. 6, the stent holder 207 can comprise a recess 208 which is configured to house a tab 8 on the extended member 7 of the prosthetic valve stent frame 3. In operation, the tab 8 on the extended member 7 of the stent 3 would be inserted into the recess 208 on the stent holder 207, and the stent holder 207 would be advanced into the valve chamber 201 to sandwich the tab 8 between the recess 208 and the inner wall of the valve chamber 201. The prosthesis 2 would be crimped around the stent holder sheath 206, and the stent holder 207 would be advanced to the distal end of the valve chamber 201 to load the crimped prosthesis 2 into the valve chamber 201. To release the prosthesis 2, the valve chamber sheath 203 would be advanced distally while keeping the stent holder 207 position fixed. In this aspect, the tab 8 would be engaged with the stent holder 207 until the valve chamber 201 had been advanced enough to reveal the recess 208 in the stent holder 207. One skilled in the art can appreciate that this recess 208 thus acts as a safety mechanism to fix the prosthesis 2 to the VHPL system 1 such that it can be positioned and maneuvered within the heart using the VHPL system 1 controls until it is selectively released.

In one aspect, the valve chamber 201 can have a plurality of slits 205 extending axially from the proximal end of the valve chamber 201 that are about one to five millimeters (1-5 mm) long. The slits 205 can be positioned on the valve chamber 201 to align with holes on the flared portion 9 of the crimped stent 3, such that following DGF member 101 implantation, the trailing DGF member tails 104 can be inserted through the slits 205 of the valve chamber 201 can be designed to correspond to the number and location of the implanted DGF members 101.

In one exemplary aspect three DGF head members 102 can be implanted in the annulus first: one at the medial commissure representing the P3 location, one at the lateral commissure representing the P1 location, and one in the center of the posterior annulus representing the P2 location. The slits 205 will be positioned along the circumference of the valve chamber 201 to align with the holes 9 on the medial edge, lateral edge, and the center of the flared portion of the crimped prosthesis 2 respectively when the crimped prosthesis 2 is loaded into the valve chamber 201, such that the trailing DGF tails 104 can easily be fed through the slits 205 and into the corresponding flare holes 9, and then through the corresponding locking catheter 317 in the VHPL system 1.

In one aspect, the VHPL system 1 can be inserted into the patient's body and the DGF member tails 104 can be tensioned to guide the valve chamber 201, and thus the valve stent, to the operative position at the previously implanted DGF members 101 once in position at the mitral annulus, the valve chamber sheath 203 can be advanced to release the prosthesis starting with the atrial flared portion 4 and continuing until the entire ventricular portion 5 of the prosthesis 2 has been released.

In one aspect, a plurality of locking catheters 317 are used to prevent proximal motion of the prosthesis 2 while the plurality of DGF member tails 104 are tensioned, in order to pull the locking member 105 on the DGF member 101 through the atrial flare hole 9 of the prosthesis 2, thereby locking the prosthesis 2 into place on the native mitral annulus. The locking catheter 317 is a composite sheath consisting, in one exemplary aspect, of three distinct sections that facilitate the fixation of the prosthesis 2. The proximal section of the locking catheter 318 can include, but not limited to, a long, rigid metal tube. The metal tube 318 can span the majority of the delivery system and can function as the control to translate the locking catheter 317 through the valve housing, positioning, and locking system handle 1. The middle portion of the locking catheter 319 can include a flexible material that conforms to the sharp curvature of the deployment pathway. The flexible portion 319 of the locking catheter 317 is able to bend equal or greater than about ninety degrees (90°) with a small bend radius to ensure locking is achievable along all parts of the annulus. The flexible portion 319 can be made of, but is not limited to, metallic, polymeric, or rubber materials of the like, and optionally can feature a coiled structure to allow for low bending rigidity and prevent the inner lumen from collapsing. The distal section of the locking catheter 320 can include a metal locking insert that engages with the locking member 105 and the atrial flared portion 4 of the prosthetic valve 2 to aid in fixing the prosthetic valve 2 at the DGF body member 103.

In one exemplary aspect, the locking catheters 317 can attach to a handle to enable an operator to grab and ease the locking process.

In one aspect, a suture tensioning mechanism can be configured to allow each of the DGF locking members 105 to be locked into place on the top of the atrial flared portion of the valve 4 independently. In this aspect, each individual DGF member tail 104 controlled in the suture tensioning mechanism, such as that shown in FIG. 10.

In one aspect, the DGF tail tension mechanism includes an assembly of ratcheting gears 96*a* and a turn knob 96. A ratcheting gear includes a round gear with teeth that can be pivoting. A spring-loaded finger component engages the teeth of the gear. The gear teeth are uniform and both slopes on the teeth are symmetrical, allowing the teeth to move in both forward and backward directions. The stiffness of the spring-loaded finger and the slope on the gear teeth will allow for controlled incremental turning of the gear and thus controlled incremental tensioning of the DGF member tail 104.

In another aspect, the gear can be configured with an asymmetrical slope to allow one directional turning, thus, preventing the DGF tail member 104 from loosening during the procedure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A heart valve leaflet replacement delivery system for treatment of a diseased heart valve within a patient's body, the system comprising: a prosthetic valve comprising a stent including an upper flared portion and a lower portion and at least one prosthetic leaflet, the stent comprising a plurality of through-holes in the upper flared portion; a plurality of dual-guiding and fixation (DGF) members; and a multi-stage, multi-lumen (MSML) delivery system comprising a dual-guiding-and-fixation (DGF) delivery system and a valve housing, positioning, and locking (VHPL) system configured cooperatively for advancing to an operative position, and for delivering and implanting the plurality of DGF members to the operative position, and for guiding, delivering, and fixing the prosthetic valve to the operative position;

wherein each of the plurality of DGF members comprises a head portion including a sharpened tip configured to be embedded in tissue, a body portion including a fixation mechanism, and a tail portion that extends from the body portion to a proximal end of the MSML system comprising a tether;

the DGF delivery system configured to implant the plurality of DGF members in a native annulus such that one end of each tail portion is attached to the respective body portion and the other end of each tail portion exits the patient's body to aid in guiding and fixing the prosthetic valve, the tail portions extending from the body portions to a proximal side of the DGF delivery system to guide prosthetic valve delivery via the plurality of through-holes; and the VHPL system configured to track over the tail portions to a desired implantation location at the previously implanted plurality of DGF members, and incrementally release the prosthetic valve from a crimped state starting with a proximal-most portion of the prosthetic valve and moving to a distal-most portion of the prosthetic valve, and fix the prosthetic valve to the plurality of DGF members via the respective fixation mechanisms, wherein the body portion of each of the plurality of DGF members is configured to attach to the respective head portion and resist separation, and each body portion is configured with a plurality of engagement structures designed to engage with the DGF delivery system, and comprises a plurality of passages, wherein at least one passage of the plurality of passages is configured for securing the respective fixation mechanism to the respective body portion, and at least one other passage of the plurality of passages is for attaching a stabilization member.

2. The system of claim 1, wherein the head portion of each of the plurality of DGF members is configured with a spiral with a length of between 4-10 mm, and a diameter of between 2 to 5 mm, formed with a wire with a diameter between 0.25-1.0 mm, and wherein each DGF member further comprises a stabilization member configured as a straight wire with a diameter between 0.25-1.0 mm extending axially through a center of the spiral with the sharpened tip extending between 1-3 mm beyond an end of the spiral.

3. The system of claim 1, wherein each of the fixation mechanisms comprises at least one locking member and at least one tether; wherein the at least one tether is configured to attach the at least one locking member to the body portion and the at least one locking member is configured to pass through one of the plurality of through-holes in the prosthetic valve in one direction only to fix the stent between the at least one locking member and a base of the body portion.

4. The system of claim 3, wherein the at least one locking member is configured with a plurality of radially compressible legs flaring outward, forming a cone or dome shape.

5. The system of claim 1, wherein the VHPL system comprises:

a valve chamber sheath including a distal end carrying a valve chamber, the valve chamber sheath extending to a proximal side of the VHPL system;

a stent holder sheath carrying, a stent holder that fits within the valve chamber is configured to travel over the valve chamber sheath and extend to the proximal side of the VHPL system;

a plurality of locking catheters positioned proximal to the stent holder and extending to the proximal side of the VHPL system; and a multi-lumen guide sheath to house the stent holder sheath and the plurality of locking catheters.

6. The system of claim 1, wherein the crimped prosthetic valve is housed within a valve chamber at a distal end of the VHPL system in a crimped delivery condition.

7. The system of claim 6, wherein the valve chamber is configured as a cylinder comprising a closed distal side, an atraumatic distal tip to prevent injury to the patient's body in operation and aid in navigation.

8. The system of claim 6, wherein the valve chamber is configured with a plurality of axial slits extending from a proximal end of the valve chamber which align with respective through-holes of the plurality of through-holes in the prosthetic valve when the prosthetic valve is crimped and loaded within the valve chamber.

9. The system of claim 6, wherein the VHPL system is configured to accommodate the tail portions of the plurality of DGF members implanted prior to the prosthetic valve delivery with a plurality of locking catheters positioned proximal to the crimped prosthetic valve in the VHPL system.

10. The system of claim 6, wherein a proximal side of the VHPL system is configured with a suture tension mechanism to individually, selectively tension the tail portions to guide the prosthetic valve delivery and fixation.

11. The system of claim 10, wherein the suture tension mechanism comprises an assembly of ratcheting gears, such that the plurality of DGF members can be selectively attached and detached from the assembly of ratcheting gears, and selectively rotating the assembly of ratcheting gears in one rotative direction increases tension in the tail portions, rotating the assembly of ratcheting gears in the other rotative direction releases tension in the tail portions, and no rotation maintains the previously attained tension in the tail portions.

12. The system of claim 1, wherein the stent is configured with at least one elongated member extending between about two and six millimeters (2-6 mm) from the lower portion of the stent, and wherein the lower portion can be configured to be straight or curved inward radially.

13. The system of claim 12, wherein the at least one elongated member is configured to selectively engage the VHPL system such that the prosthetic valve can be guided, expanded, and fixed in position at the plurality of DGF members before selectively detaching the prosthetic valve from the VHPL system.

14. The system of claim 13, wherein at least one tab at a distal tip of the at least one elongated member is configured to fit within at least one recess in a stent holder positioned distal to the prosthetic valve when the prosthetic valve is crimped within a valve chamber, such that the prosthetic valve can be selectively attached to the VHPL system by putting the at least one tab within the at least one recess in the stent holder and inserting the stent holder into the valve chamber such that the at least one tab is sandwiched between an inner wall of the valve chamber and the at least one recess in the stent holder, and the prosthetic valve can be selectively detached from the VHPL system by advancing the valve chamber distally relative to the stent holder to uncover the at least one recess in the stent holder and release the at least one tab.

15. The system of claim 1, wherein the head portion of each of the plurality of DGF members is configured to implant through the upper flared portion of the stent, such that a plurality of additional DGF members can be implanted on top of the prosthetic valve in the operative position after it has been fixed in place by a plurality of previously implanted DGF members with DGF locking members.

16. The system of claim 1, wherein the head portion of each DGF member comprises one of a spiral shape, a coil shape, and a screw shape configured to screw the head portion into tissue adjacent the annulus.

17. The system of claim 1, wherein each of the plurality of DGF members comprises a locking member spaced apart from a base of the body portion such that the upper flared portion fits snugly between the locking member and the base of the body portion in the operative position.

18. The system of claim 17, wherein the plurality of through-holes are spaced apart in a circular shape connecting cell struts and forming a bridge connection with neighboring cells defining the upper flared portion.

19. The system of claim 17, wherein the locking member of each of the plurality of DGF members comprises a proximal portion and an expandable distal portion configured to pass distally through one of the plurality of through-holes in the prosthetic valve in one direction only to fix the stent between the locking member and the body portion.

20. A heart valve leaflet replacement delivery system for treatment of a diseased heart valve, the system comprising:

a prosthetic valve comprising a stent and at least one prosthetic leaflet, the stent comprising a plurality of through-holes;

a multi-stage, multi-lumen (MSML) delivery system comprising a dual-guiding-and-fixation (DGF) delivery system and a valve housing, positioning, and locking (VHPL) system configured cooperatively for advancing to an operative position, and for delivering and implanting a plurality of DGF members to the operative position, and for guiding, delivering, and fixing the prosthetic valve to the operative position;

the DGF delivery system configured to implant the plurality of DGF members in a native annulus to aid in guiding and fixing the prosthetic valve; wherein each of the plurality of DGF members comprises a head portion configured to be embedded in tissue, a body portion including a fixation mechanism, and a tail portion that extends from the body portion to a proximal side of the DGF delivery system to guide prosthetic valve delivery via the plurality of through-holes; and the VHPL system configured to track the tail portions to a desired implantation location at the previously implanted DGF members, incrementally release the prosthetic valve from a crimped state starting with a proximal-most portion of the prosthetic valve and moving to a distal-most portion of the prosthetic valve, and fix the prosthetic valve to the DGF members via the respective fixation mechanisms, wherein each of the fixation mechanisms comprises at least one locking member and at least one tether; wherein the at least one tether is configured to attach the at least one locking member to the respective body portion and the at least locking member is configured to pass through one of the plurality of through-holes in the prosthetic valve in one direction only, and wherein the at least one locking member is attached to the respective body portion via a tether of the at least one tether that is looped through passages in the respective body portion, wherein the tether of the at least one tether is configured with a proximal loop for selectively attaching the tail portion of a respective DGF member of the plurality of DGF members.

* * * * *